US012611118B1

(12) United States Patent
Hayes et al.

(10) Patent No.: US 12,611,118 B1
(45) Date of Patent: Apr. 28, 2026

(54) MODULAR BREATH TRACKING AND TRAINING SYSTEM

(71) Applicants:Robert Ira Hayes, San Diego, CA (US); Russell E Allen, San Diego, CA (US)

(72) Inventors: Robert Ira Hayes, San Diego, CA (US); Russell E Allen, San Diego, CA (US)

( * ) Notice: Subject to any disclaimer, the term of this patent is extended or adjusted under 35 U.S.C. 154(b) by 0 days.

(21) Appl. No.: 19/047,451

(22) Filed: Feb. 6, 2025

Related U.S. Application Data

(60) Provisional application No. 63/551,063, filed on Feb. 7, 2024.

(51) Int. Cl.
| | |
|---|---|
| *A61B 5/097* | (2006.01) |
| *A61B 5/00* | (2006.01) |
| *A61B 5/087* | (2006.01) |
| *A61B 5/09* | (2006.01) |
| *A61B 5/091* | (2006.01) |
| *A63B 23/18* | (2006.01) |

(52) U.S. Cl.
CPC ............ *A61B 5/097* (2013.01); *A61B 5/0004* (2013.01); *A61B 5/0873* (2013.01); *A61B 5/09* (2013.01); *A61B 5/091* (2013.01); *A61B 5/7445* (2013.01); *A63B 23/18* (2013.01); *A61B 2560/0214* (2013.01); *A61B 2560/0443* (2013.01); *A61B 2562/0219* (2013.01); *A61B 2562/12* (2013.01); *A61B 2562/166* (2013.01)

(58) Field of Classification Search
None
See application file for complete search history.

(56) References Cited

U.S. PATENT DOCUMENTS

| | | | | |
|---|---|---|---|---|
| 8,753,286 B2* | 6/2014 | Scholz | ................... | A61B 5/087 |
| | | | | 600/533 |
| 11,617,920 B2 | 4/2023 | Poulsen et al. | | |
| 2012/0029376 A1* | 2/2012 | Meng | ................... | A61B 5/7475 |
| | | | | 600/538 |
| 2014/0303451 A1* | 10/2014 | Beiswenger | ............. | A61B 5/09 |
| | | | | 600/301 |
| 2015/0005639 A1* | 1/2015 | Blanton | ................. | A61B 5/082 |
| | | | | 73/23.3 |

(Continued)

OTHER PUBLICATIONS

Spirolink User Manual Model B1, No publication date, printed out from www.cmihealth.com/products/spirolink on Feb. 6, 2025, 15 pgs.

(Continued)

*Primary Examiner* — Jacqueline Cheng
*Assistant Examiner* — Samuel C Kim
(74) *Attorney, Agent, or Firm* — Advantage IP Law Firm

(57) ABSTRACT

A modular breath tracking and training system having a primary housing with an interactive airway chamber with an airflow responsive element in the airflow path of the chamber with at least one sensor element positioned to detect signals from the airflow responsive element with the primary housing being removably coupled to at least one respiratory orifice interface and operable to direct air between at least one respiratory orifice and the interactive airway chamber of the primary housing during use wherein a user may be guided to perform one or more breathwork exercises through one or more feedback devices.

27 Claims, 19 Drawing Sheets

(56)     References Cited

U.S. PATENT DOCUMENTS

| | | | |
|---|---|---|---|
| 2019/0175065 A1* | 6/2019 | Knestel .................. | A61B 5/097 |
| 2019/0350466 A1* | 11/2019 | Boschetti Sacco .. | A61B 5/7264 |
| 2020/0330719 A1* | 10/2020 | Segal .................. | A61M 15/008 |
| 2021/0001169 A1* | 1/2021 | Roussel .............. | A61M 16/201 |
| 2021/0085247 A1* | 3/2021 | Meirav ................ | A61B 5/0833 |
| 2024/0149111 A1 | 5/2024 | Poulsen et al. | |

OTHER PUBLICATIONS

MIR Spirobank II Smart Technical Data Sheet, no publication date, printed out from https://spirometry.com/en/products/spirobank-ii-smart on Feb. 6, 2025, 1pg.
MIR Spirobank Il Brochure, no publication date, printed out from https://spirometry.com/en/products/spirobank-ii-smart on Feb. 6, 2025, 8 pgs.

\* cited by examiner

MODULAR BREATH TRACKING AND TRAINING SYSTEM

CROSS-REFERENCE TO OTHER APPLICATIONS

This application claims the benefit of U.S. provisional patent Application No. 63/551,063, filed on Feb. 7, 2024, titled Modular Breath Tracking and Training Device, and which is hereby incorporated by reference in its entirety.

BACKGROUND

1. Field of the Disclosure

The disclosure relates broadly to health monitoring devices, respiratory therapy equipment, and Internet of Things (IoT) applications in personal health technology, and more specifically, to improvements in breathwork detection and training systems.

2. Background Art

Effective breath control and respiratory training are crucial for enhancing physical performance, managing stress, and improving health. Devices for sensing and measuring lung capacity and related respiratory parameters have been in development for centuries. One such device for measuring lung capacity is the spirometer. Early examples include directing a patient to take a deep breath and then exhale through a mouthpiece connected to a tank filled with water having some sort of calibrated weighted device therein. For example, one particular water spirometer, invented by a surgeon John Hutchinson, included a calibrated bell inverted in the water which was used to capture the volume of air exhaled by a person. This construction allowed for measuring vital (lung) capacity, an early scientific based parameter for determining lung health.

During hospital stays, a simple rehabilitation spirometer typically includes a plastic housing with one or more movable elements positioned within one or more cylindrical chambers. The movable element is often a piston, plastic ball, or weighted object. The chamber or chambers are filled with either air or water. The chamber may have graduated or target markings indicated thereon as a source of measurement. A mouthpiece and tube are attached to the chamber. The user would then grasp hold of the mouthpiece and exhale or inhale (uni-directional) through the tube to move the ball to the designated target and hold for a period of time. This is repeated to help strengthen the lungs of the patient and is especially used for those restricted to bedrest or recovering from lung related maladies.

In addition to the benefits of exercising a user's lungs while in hospital stays, more recently there's been a focus on breath training and breath analyzers as either therapeutic, stress management, or as exercise and athletic performance aids. In one example, a user dons a mask while performing an exercise, such as running. The mask includes some sort of restrictive element to make the user's lung work harder than without the mask. Then, over time when the mask is removed, the user may find the same exercise easier to perform. Such performance enhancing aids typically benefit the user by inserting a resistance element or otherwise restricting airflow to the user forcing the user to do more with less oxygen (use oxygen intake more efficiently) while using the device, essentially replicating high altitude training. The mask may be adjustable to define different altitudes by varying resistance or somewhat constricting external airflow. However, such devices are typically either connected to a bulky oxygen supply system or a heavy backpack or worn as a simple mask that does not measure or supply any metrics or feedback.

More recent efforts have seen the lung capacity measuring and improvement technologies move toward more sophisticated spirometers and breath training devices, including "smart" spirometers. However, many of these devices suffer from only measuring airflow parameters based solely on exhalation processes, completely ignoring the inhalation process. Devices that take into account both inhalation and exhalation processes are less common.

One such device that measures both inhalation and exhalation related airflow data may be found in U.S. Pat. No. 11,617,920 to Poulsen et al. This device includes a separate inhalation chamber and a separate exhalation chamber with their own distinct external ports, both converging into a common chamber leading to a mouthpiece. The outer extent of the inhalation chamber includes an inhalation port with a dedicated inhalation resistance dial for altering the resistance of the air flow entering the inhalation port. Similarly, the outer extent of the exhalation chamber includes an exhalation port with a dedicated exhalation resistance dial for altering resistance of the air flow exiting the exhalation port. One-way valves in each chamber dictate the respective inhalation and exhalation resistance pathways. Airflow moving across a common pressure gauge sensor is sensed to provide airflow pressure data. A processing unit is included for collecting and storing and transmitting the air pressure data. The device may communicate with a remote device such as a smart phone. However, such a device is focused solely on presenting a resistance based training exercise, requires separate exhalation and inhalation sections, and has no onboard feedback or training prompt features, instead relying on a remote device to provide the user interface.

Another main drawback of many of these devices is the lack of modularity or use across a variety of fitments or respiratory orifice interfaces. In addition, such devices lack on-board multi-sensory feedback such as a combination of one or more sensory devices providing visual, audible, spatial orientation, and haptic feedback and/or training prompts. Prior methods often lack the precision, personalization, and interactive feedback necessary for optimal outcomes. The advent of IoT technology presents an opportunity to revolutionize this domain through smart, standalone or connected devices that offer a more effective, user-friendly approach to breath training and monitoring. Given the drawbacks of the prior approaches, there exists a need for an improved breath tracking and training system that provides instant feedback and guidance concerning the user's breathwork experience among other advantages.

SUMMARY

In accordance with one or more embodiments a modular breath tracking and training system is disclosed herein with a primary housing with an interactive airway chamber passing therethrough, the interactive airway chamber including an airflow responsive element and at least one sensor element constructed to detect one or more airflow related parameters based on interaction with the airflow responsive element, the system further including and at least one respiratory orifice interface constructed to removably couple to the primary housing to direct air between at least one respiratory orifice and the interactive airway chamber of the primary housing during use.

In another embodiment, at least a portion of the interactive airway chamber is removably coupled to the primary housing wherein the interactive airway chamber may be swapped out for an alternative portion of or the entire interactive airway chamber.

Another feature of one or more of the embodiments disclosed herein is the modular construction of the modular breath tracking and training system wherein the primary housing may be removably coupled to a variety of respiratory orifice interfaces, including, but not limited to, a mouthpiece, a mask, and a wind instrument mouthpiece.

Yet another feature of one or more of the embodiments disclosed herein is the incorporation of a fan as the airflow responsive element in the interactive airway chamber.

In another embodiment, the sensor elements include one or more optical sensors operating in conjunction with a light source to determine the airflow responsive element direction and rotation is disclosed.

In yet another embodiment, one or more feedback and/or prompting devices are included in the system to guide the user during training sessions.

In yet another embodiment, the modular breath tracking and training system is operable to communicate with a remote device to expand its capabilities.

Methods for assembling and using the modular breath tracking and training system are also disclosed herein.

Various objects, features, aspects, and advantages of embodiments will become more apparent from the following detailed description of preferred embodiments of the invention, along with the accompanying drawings in which like numerals represent like components.

BRIEF DESCRIPTION OF THE DRAWINGS

One or more modular breath tracking and training systems, and methods relating thereto are described herein with reference to the following drawings of preferred embodiments, which are intended to illustrate and not to limit the present disclosure.

DETAILED DESCRIPTION OF THE PREFERRED EMBODIMENTS

Figure 1:
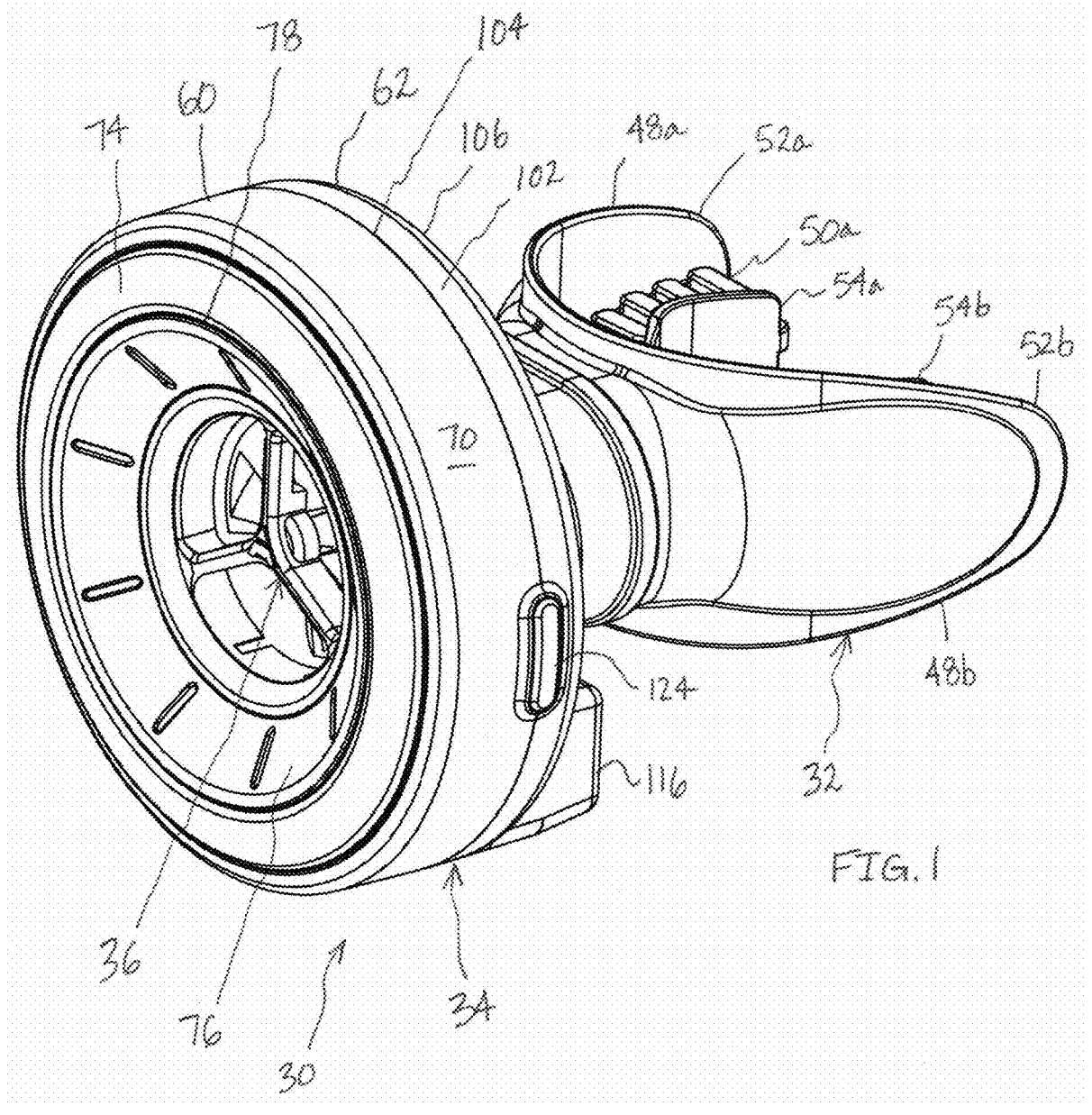
FIG. 1 is a front perspective of an exemplary modular breath tracking and training system.
Figure 2:
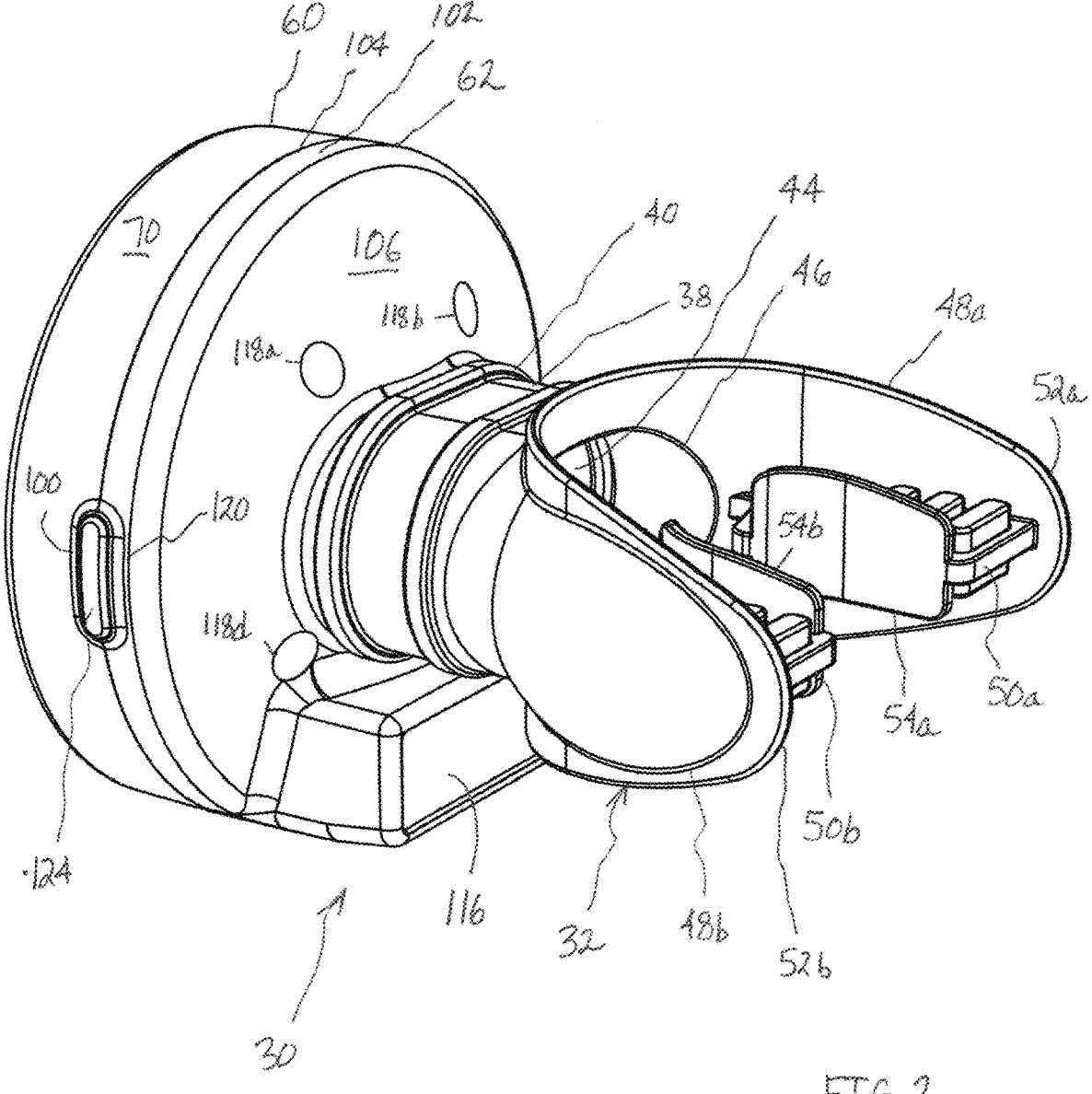
FIG. 2 is a rear perspective view thereof.
Figure 3:
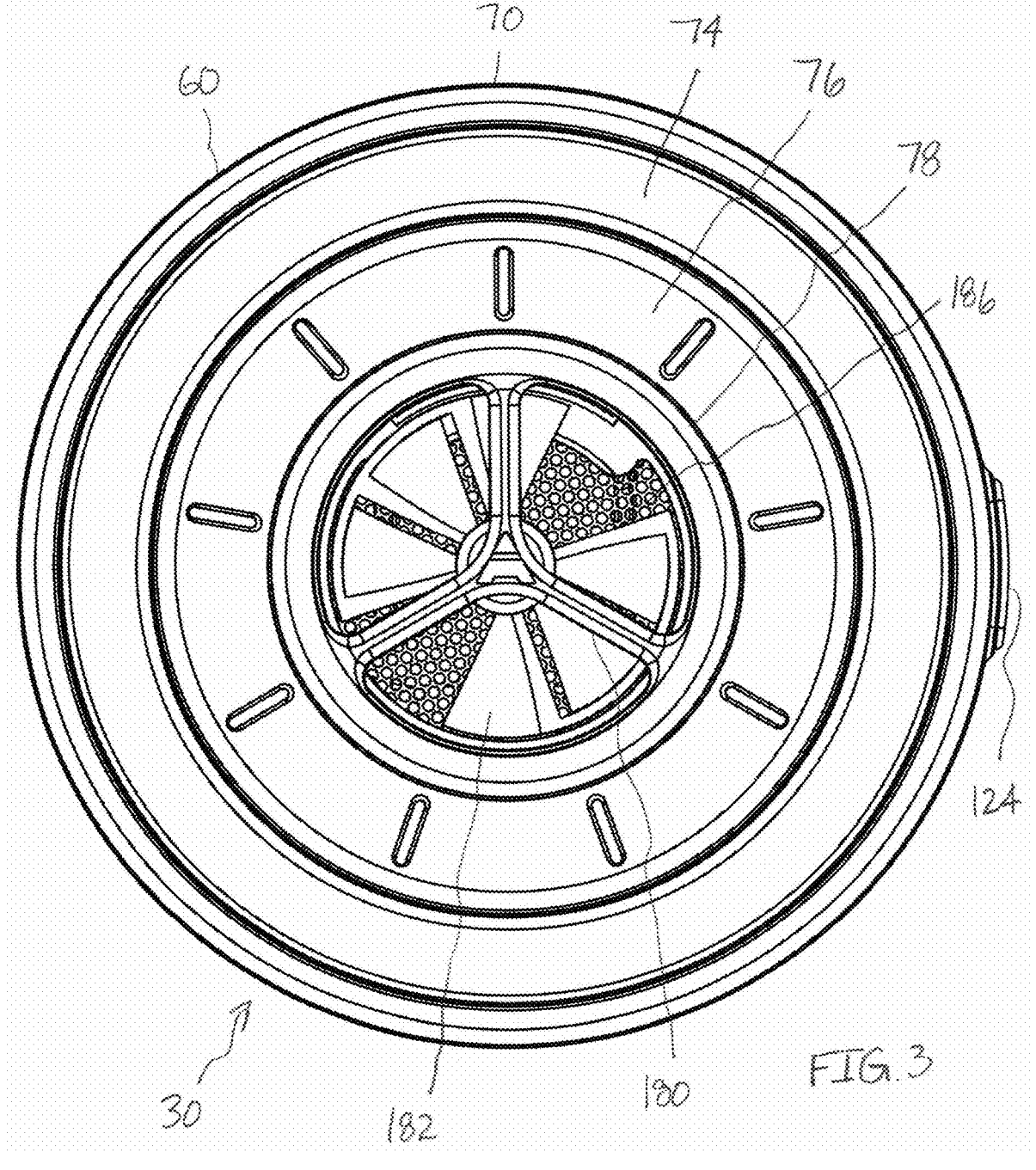
FIG. 3 is a front orthographic view thereof, in enlarged scale.
Figure 4:
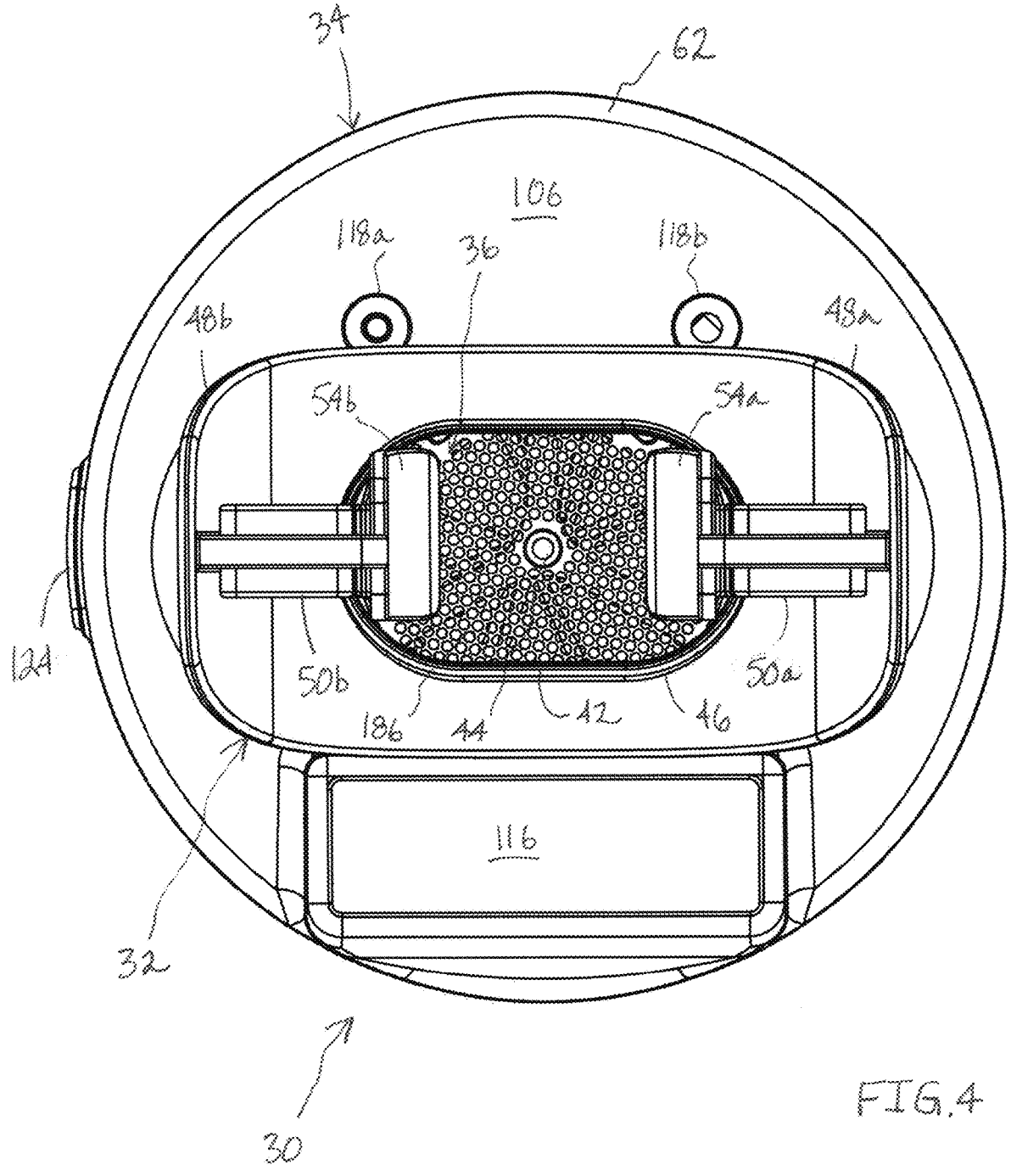
FIG. 4 is a rear orthographic view thereof, in enlarged scale.
Figure 5:
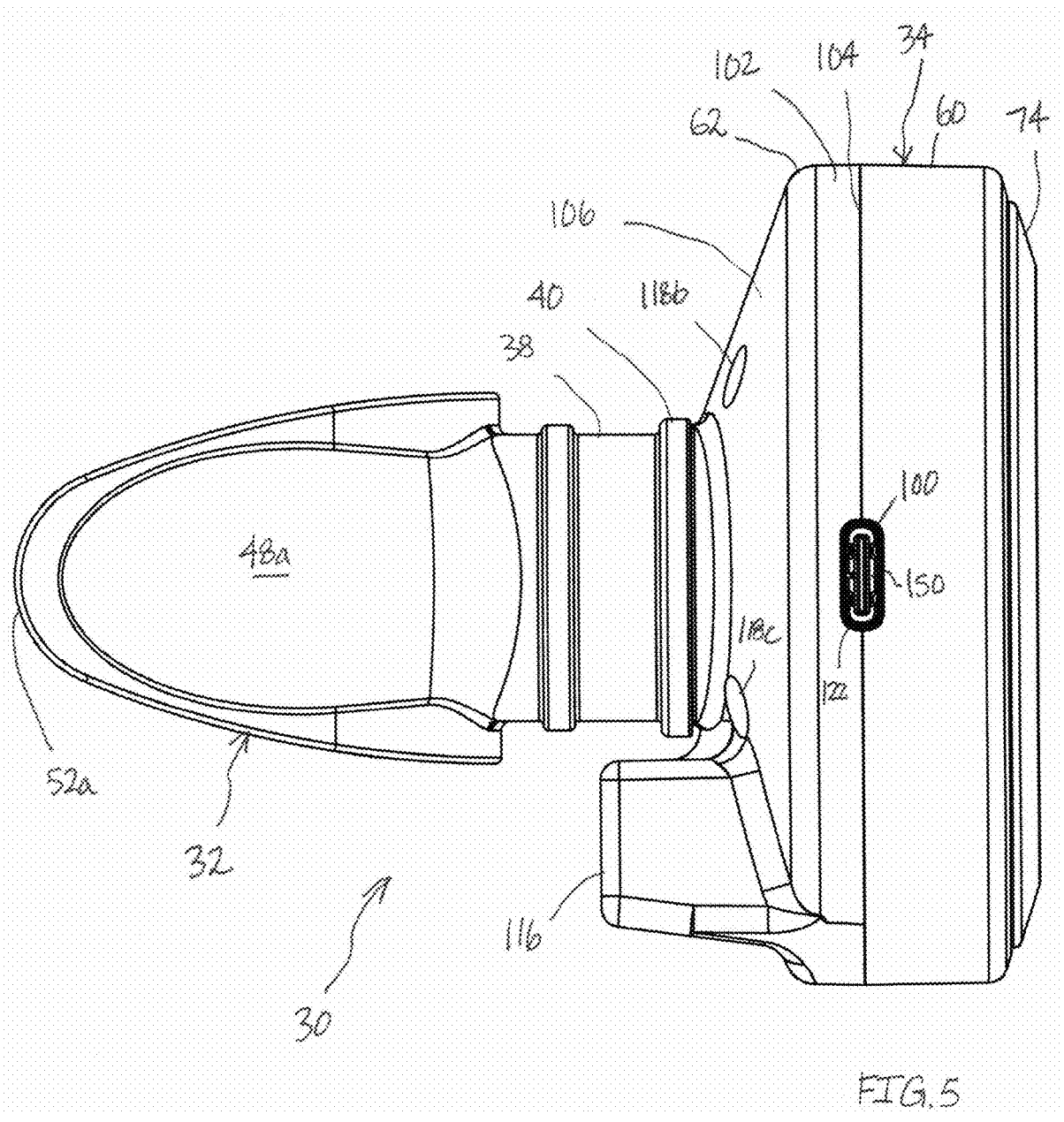
FIG. 5 is a left side orthographic view thereof, in enlarged scale.
Figure 6:
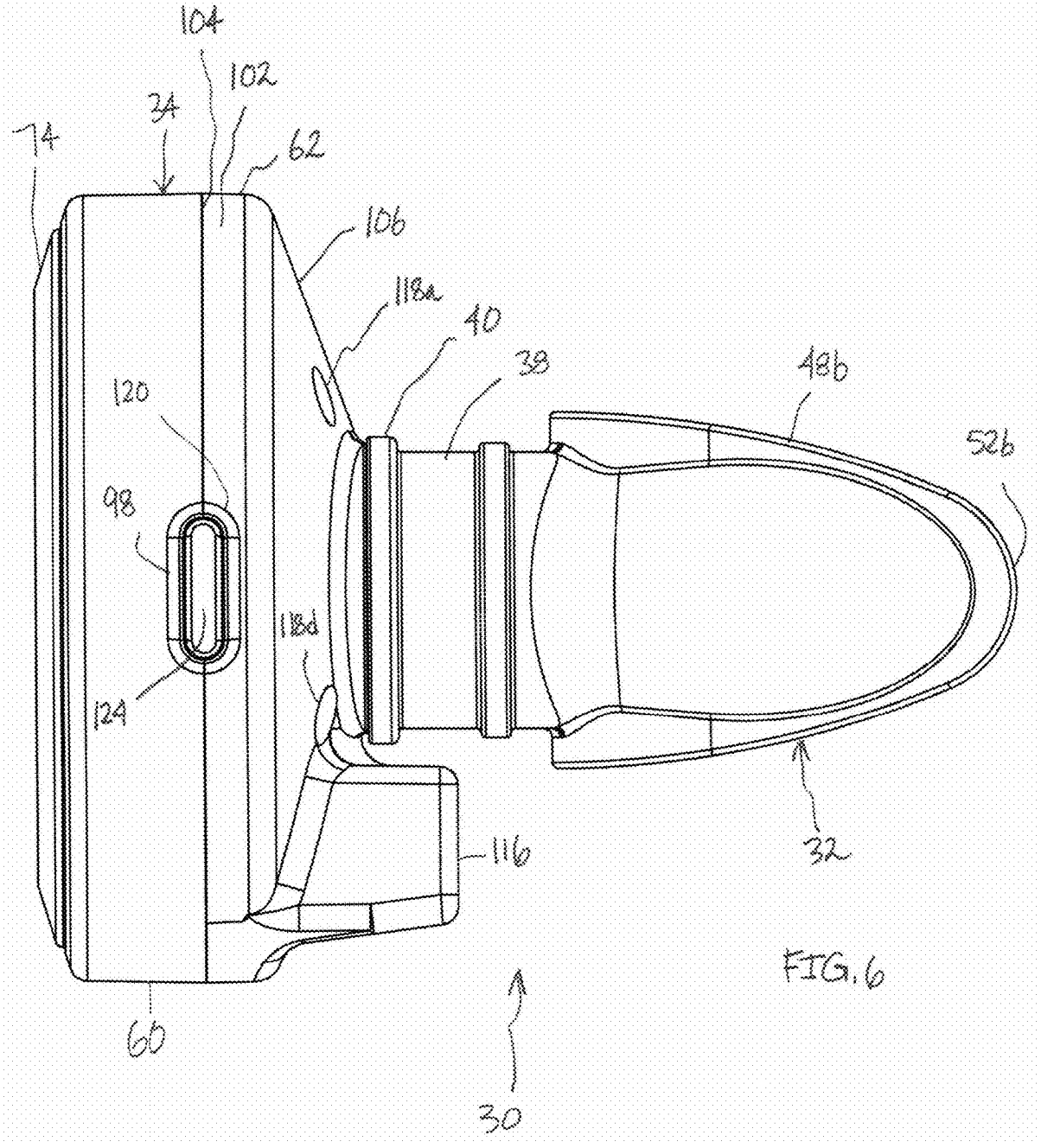
FIG. 6 is a right side orthographic view thereof, in enlarged scale.
Figure 7:
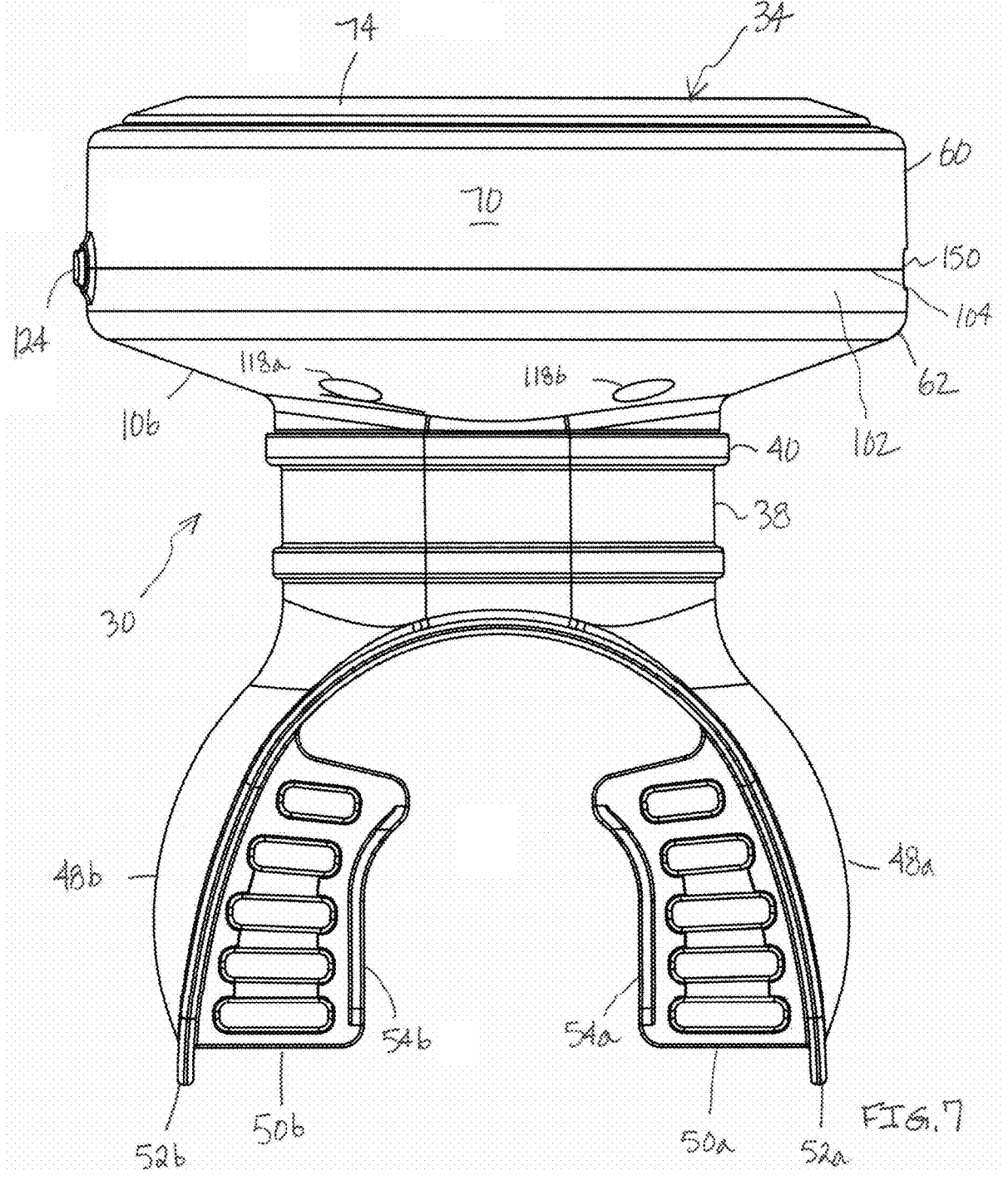
FIG. 7 is a top orthographic view thereof, in enlarged scale.
Figure 8:
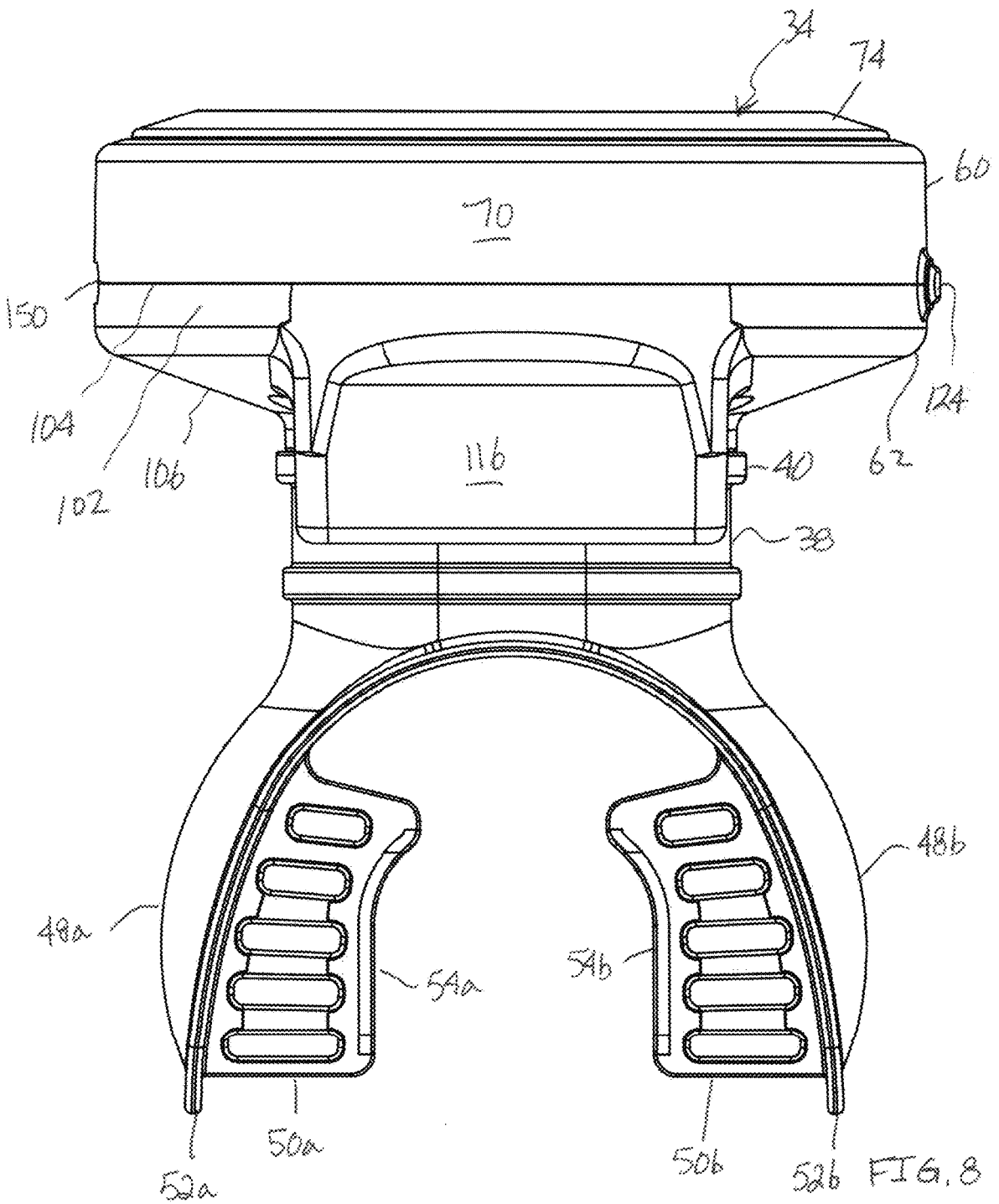
FIG. 8 is a bottom orthographic view thereof, in enlarged scale.

As described below, a modular breath tracking and training system, generally designated 30, may be provided in the form of a standalone device or a smart IoT connected breathwork tracker and trainer designed to employ a sensor pack or suite and one or more ergonomic respiratory orifice attachments, the system being tailored to measure and enhance a user's breathing capabilities. The system may further incorporate intuitive software and one or more user interfaces that seamlessly integrate with the hardware components to offer personalized breathing exercises and progress tracking through advanced analytics. The system may be programmed to adapt to the user's unique respiratory patterns, provide a customized training experience aimed at improving lung capacity, breath control, and overall respiratory health. Use based applications that may be implemented by the system 30 include, but are not limited to, stress management, athletic and exercise performance enhancement, and respiratory health management, all with an aim of improving and optimizing respiratory fitness and the related benefits from achieving such fitness.

In at least one form, the system 30 may provide a degree of connectivity to render the system an IoT (Internet of Things) enabled modular breath tracking and training system. The system is designed to monitor, analyze, and improve breathing patterns in real-time, offering users a comprehensive solution for respiratory health and performance enhancement. Integrating advanced sensors, wireless connectivity, and a versatile software platform, the system 30 is capable of providing personalized breathing exercises, feedback, and progress tracking to promote optimal breathing techniques and overall well-being.

In general terms, embodiments of one or more modular breath tracking and training systems, and methods of using such systems are disclosed herein. In the non-limiting examples given below, the modular breath tracking and training system may be used to sense or track a user's breathwork as well as train or prompt the user to use the system in a particular manner to improve lung capacity and respiratory muscle strength facilitating an improvement in overall breathing quality and efficiency and related advantages of having achieved such improvements. In addition, the preferred modular construction of such a system allows for use across a variety of respiratory interface devices as well as different sensor packs and airflow interactive devices.

Referring initially to FIGS. 1-9, a first exemplary embodiment of a modular breath tracking and training system, generally designated 30, is depicted. The modular breath tracking and training system 30 generally includes three primary components: a respiratory orifice interface generally designated 32, a primary housing generally designated 34, and an interactive airway chamber generally designated 36. In general, these three components may be assembled together and cooperate to direct a user's inhalations and exhalations through a sensor chamber constructed to detect both the direction of the airflow passing through and the associated flow rate, among other data, wherein such data may be used to establish a baseline. With a baseline captured, the system may further be used to establish goals and provide training prompts to improve upon such baseline or other goals set by the user or training program.

In general terms, the respiratory orifice interface 32 operates to seal off a user's respiratory orifice producing the breathwork, the user's mouth in this example, and then capture and funnel the user's breath or airflow, whether inhaling or exhaling, and direct the airflow or retrieve the airflow from the next component of the modular breath tracking and training system 30, referring to the primary housing 34.

More specifically and as best shown in FIGS. 4, 7-8, and 10, the respiratory orifice interface 32 in this first exemplary embodiment, is provided in the form of a mouthpiece somewhat similar to a conventional scuba diving mouthpiece. More specifically, the mouthpiece includes a distal racetrack shaped mounting section 38 surrounded by an enlarged flange 40 and defining a distal opening 42. In describing the construction of the system 30 herein, the terms outermost, innermost, distal, and proximal per component 32, 34, and 36 are relative to a user's respiratory orifice when the device is placed in use. An airflow transfer channel 44 projects inwardly from the distal opening 42 through the mounting section 38 to terminate in a respiratory side opening 46 (FIGS. 2 and 4) that is constructed to be disposed at or proximate a respiratory orifice such as the user's mouth in this example. Surrounding and extending from the respiratory side opening are a pair of opposing bite wings 48a, 48b. The bite wings curve outwardly and rearwardly from the respiratory side opening. Each bite wing 48a, 48b includes an inwardly projecting cantilevered bite grip 50a, 50b, respectively. Such bite grips 50a, 50b provide a location onto which a user may bite down to place the user's teeth directly in contact with the bite grips to grip the mouthpiece while still establishing a slight gap through which the user may exhale and inhale through the respiratory side opening 46 and through the airflow transfer channel 44 and through the distal opening 42. The bite wings further include a pair of extensions 52a, 52b that extend rearwardly beyond the innermost extent of the bite grips to provide a better seal around the user's mouth. The interior surface of the bite grips 50a, 50b also include a vertically extending sealing flanges 54a, 54b, respectively, that taper inwardly proximate the respiratory side opening 46 to facilitate channeling the breathwork into and from the respiratory side opening.

Figure 12:
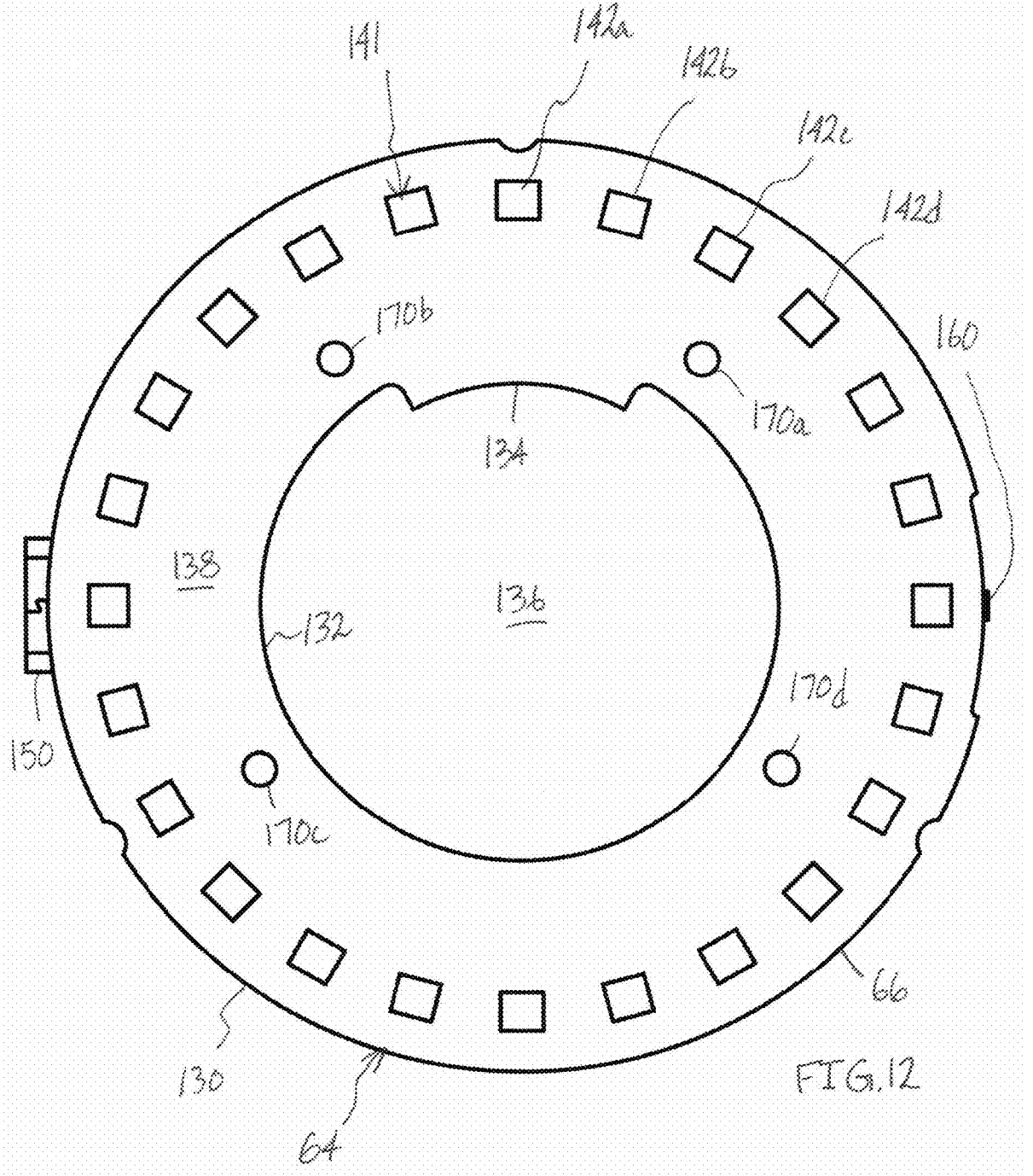
FIG. 12 is a front orthogonal view of an exemplary printed circuit board of FIG. 10, in enlarged scale.
Figure 13:
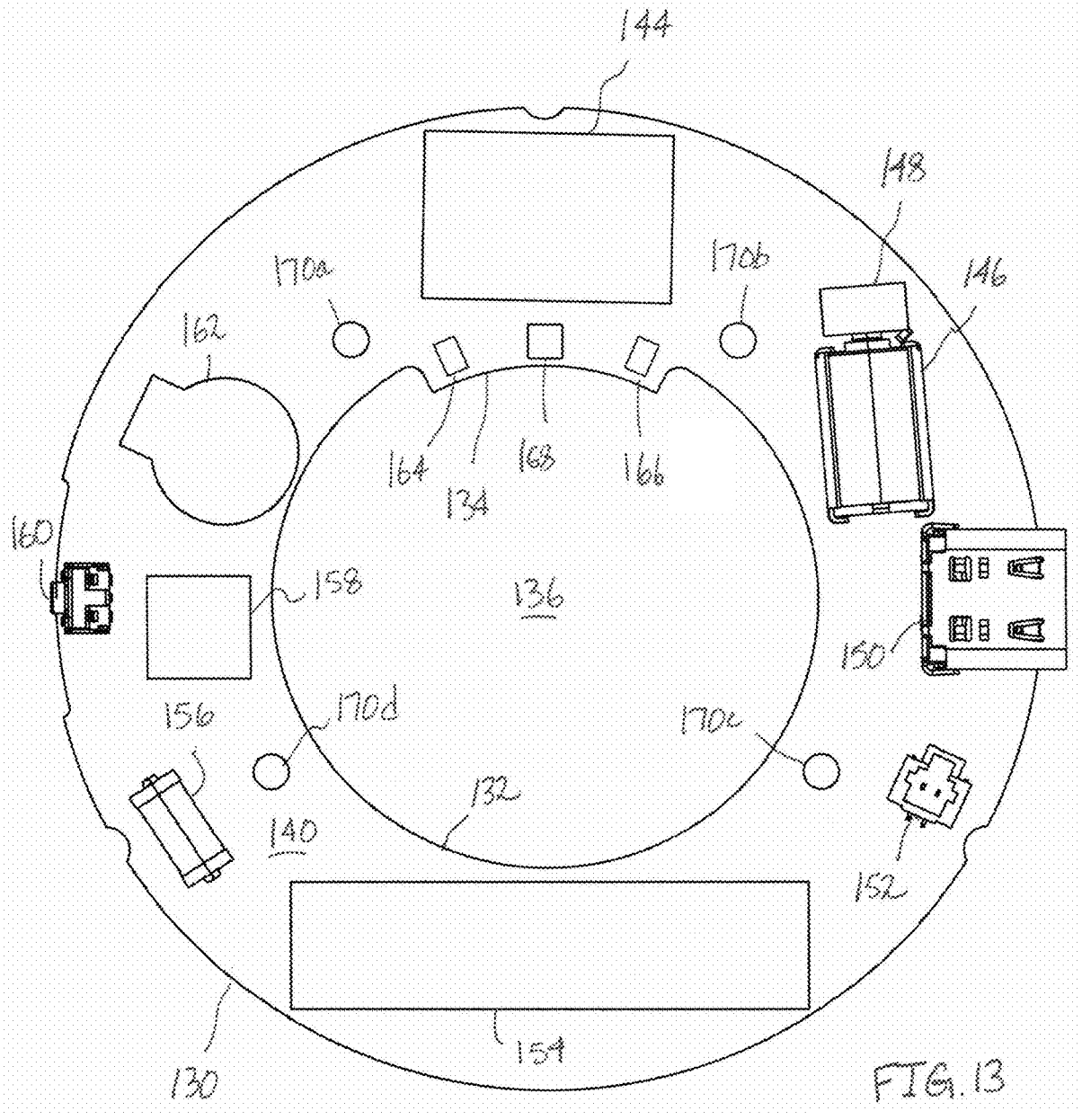
FIG. 13 is a rear orthogonal view of the printed circuit board of FIG. 12, in enlarged scale.

Turning now to FIGS. 1-13, the primary housing sub-assembly 34 includes a front or outermost section 60 and rear or innermost section 62 that cooperate to join together and enclose and protect an electronic processing device 64 depicted as a printed circuit board assembly (PCBA) or dynamic circuit with a PCB substrate (static board) 66 in FIG. 13 and a power source 68 depicted as an onboard battery in FIG. 13 as well. It will be appreciated that the primary housing sub-assembly 34 may provide all or a portion of the "brains" or "smart" aspect of the system.

As shown in FIGS. 1-10 and 13-14, the outermost section 60 is a generally cylindrical shaped component with a peripheral sidewall 70 and an outermost face 72. Disposed within the outermost face 72 is an outer ring 74 presenting an outwardly facing circular feedback visual indicator in the form of a light ring that circumnavigates the outer face of the outermost section 60. Located radially inwardly from the outer ring 74 is an inner ring 76 that tapers inwardly toward a central opening 78. The tapering of the inner ring facilitates funneling inhalations toward the central opening 78 or expanding exhalations to disperse outside the modular breath tracking and training system 30. Such central opening 78 also provides an opening through which the turbine sub-assembly 36 may be slipped through to releasably couple with the primary housing 34 as explained in further detail below. The tapering of the inner ring 76 also assists in guiding and centering the turbine sub-assembly during insertion into the primary housing 34.

Figure 9:
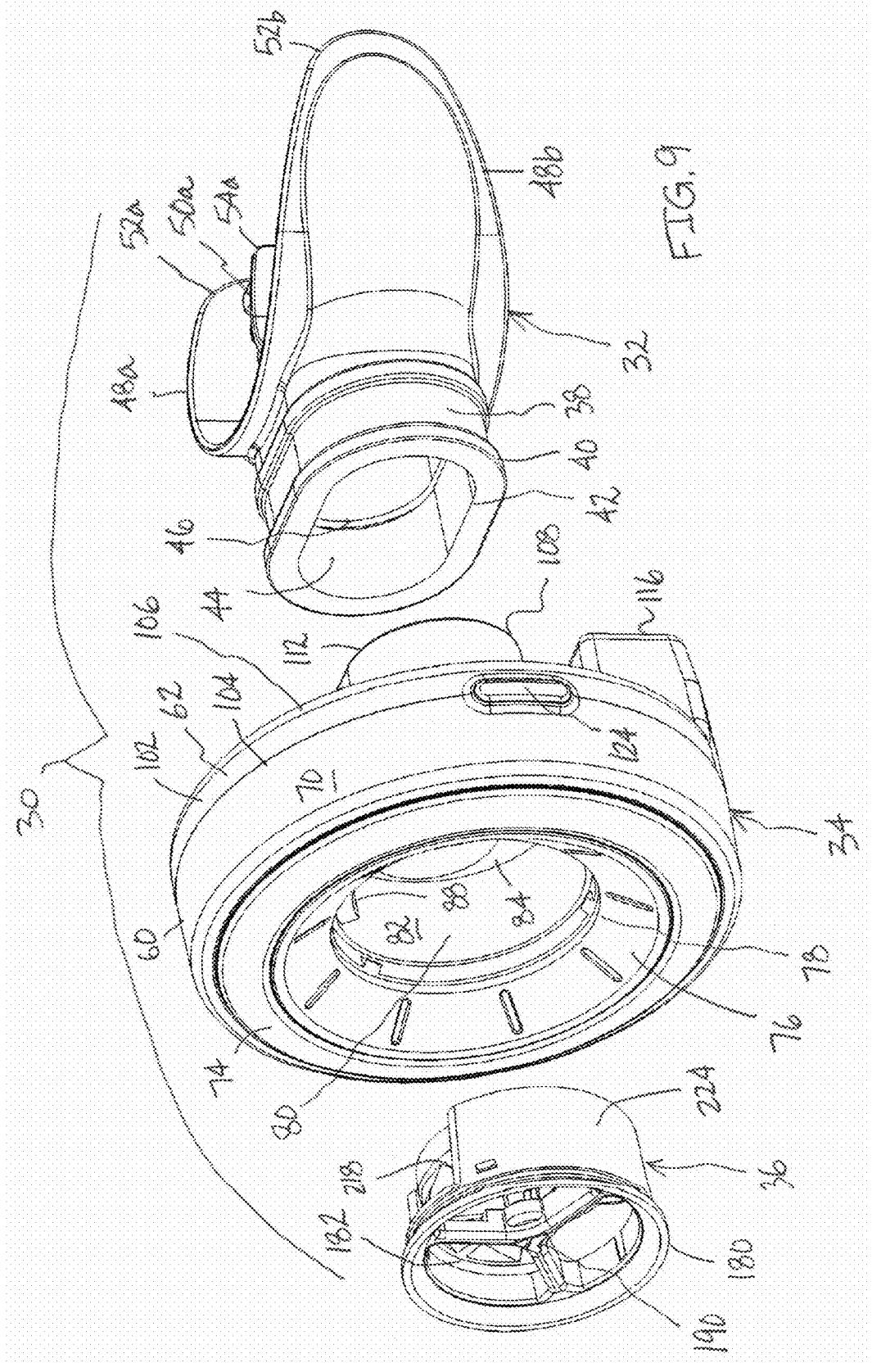
FIG. 9 is an exploded view of three exemplary primary components of the modular breath tracking and training system including a turbine sub-assembly, a housing sub-assembly, and a mouthpiece of FIG. 1, in reduced scale.
Figure 10:
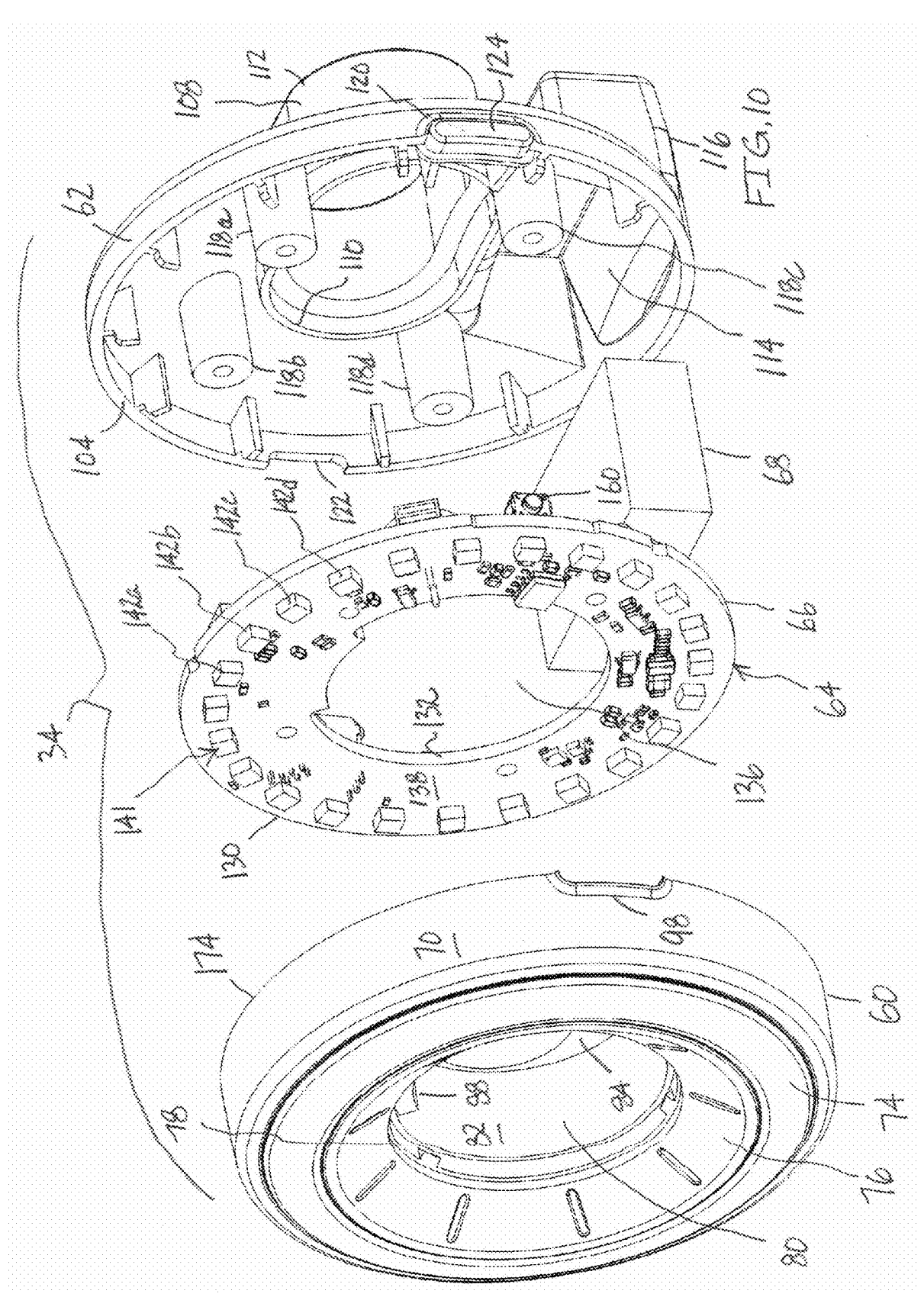
FIG. 10 is an exploded perspective view of the housing sub-assembly from FIG. 9.

With continued reference to FIGS. 9-10, the central opening 78 extends rearwardly to define a turbine sub-assembly receiving recess 80 bounded by a peripheral sidewall 82 that terminates in an innermost seat wall 84 for abuttingly receiving the inner end of the turbine sub-assembly 36. Within the innermost seat wall 84 is a racetrack shaped opening 86 (FIG. 11) maintaining an airflow passage through the outermost section 60. Protruding from the innermost seat wall 84 is an arched section 88 spanning across an arc at the top circumference of the innermost seat wall. The arched section 88 defines an alignment tooth for orienting the turbine sub-assembly in a particular position relative to the primary housing 34.

Figure 11:
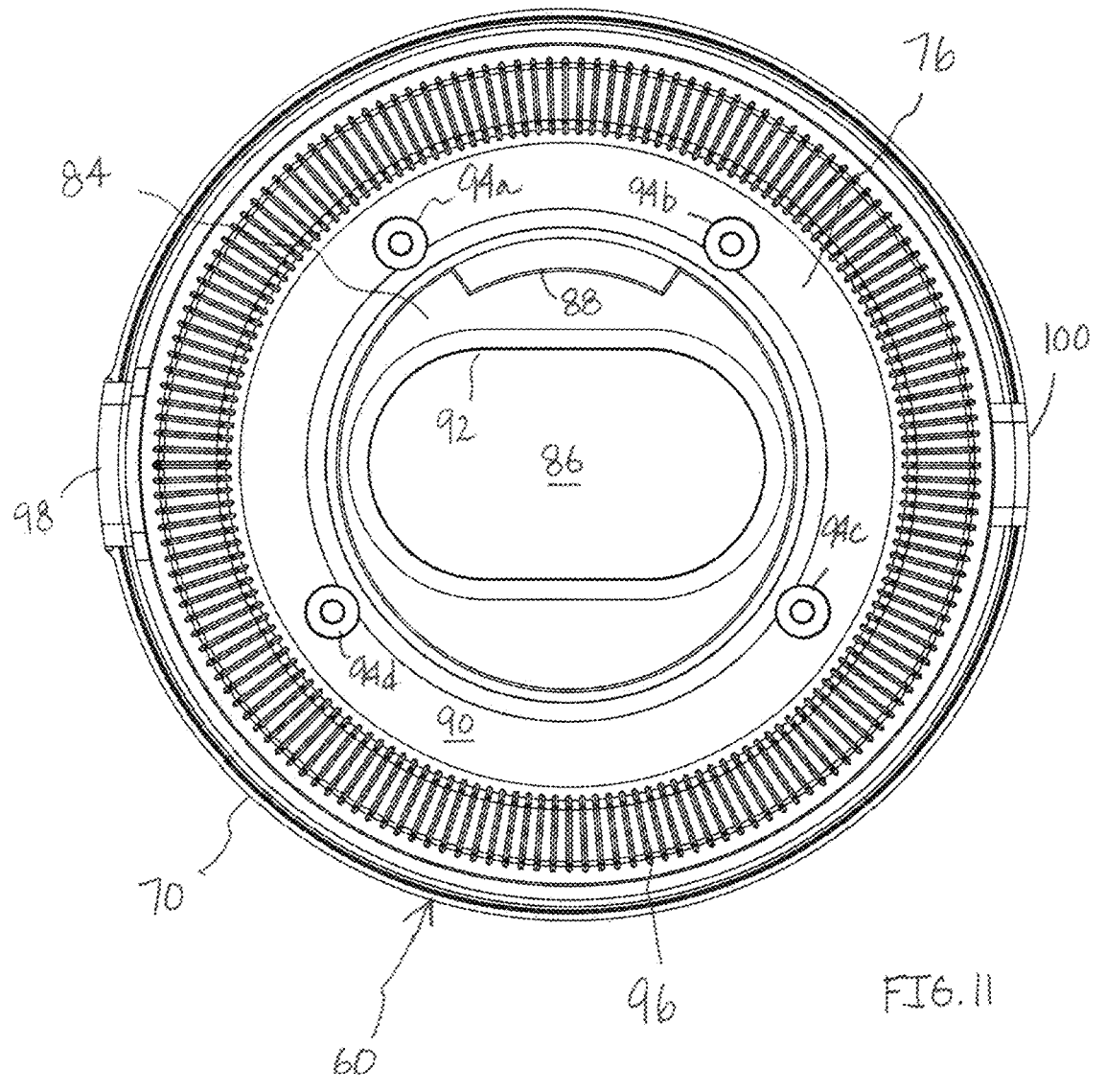
FIG. 11 is a front orthographic view of the interior surface of the front piece of the housing sub-assembly, in enlarged scale.

With reference to FIG. 11, the outermost section 60 further includes an interior surface 90 surrounding the racetrack shaped opening 86. An inwardly protruding flange 92 defines a perimeter of the opening 86 and is used for aligning the outermost section 60 with a complementary shaped section 110 (FIG. 10) of the innermost section 62. A set of four spaced apart threaded fastener receiving posts 94a-d is provided within the inner ring area 76. The interior surface of the outer ring area 74 includes a light diffuser surface 96. One-half of a push button slot 98 appears at the nine o'clock position with one-half of a USB charging port 100 appears at the three o-clock position as best shown in FIG. 11.

Turning now to FIGS. 9-10, the innermost section 62 of the primary housing 34 is also generally cylindrically shaped with a peripheral sidewall 102 having a leading edge 104 and rear wall 106 that tapers inwardly toward a rearwardly extending racetrack shaped tube 108 having a distal opening 110 disposed within the innermost section and a proximal opening 112. The interior surface 114 of the innermost section at the six o'clock position bulges rearwardly to define a battery receiving compartment 116. In addition, a set of four hollow fastener posts 118a-d provide guides for threaded fasteners (not shown) to pass through and engage threaded fasteners receiving receptacles 94a-d, respectively, projecting from the interior facing surface 90 of the outermost section 60. A power source such as a rechargeable lithium ion battery 68 may be inserted into the battery receiving compartment 116. When facing the interior surface 114 of the innermost section 62, one-half of a push button slot 120 is positioned at the three o'clock position while one-half of a USB connector slot 122 is positioned at the nine o-clock position.

Turning now to FIGS. 10 and 12-13, the PCBA 64 will now be described in more detail. In general terms, the PCBA provides an integrated tech pack including one or more sensors for measuring respiratory parameters. In this exemplary embodiment, the PCBA is a ring shaped disc or substrate 66 with a circular outermost perimeter 130 and an interior perimeter 132 that is generally circular but includes an upper edge alignment tooth 134 protruding into a central opening 136 defined by the interior perimeter 132 through which airflow may pass bi-directionally. The disc 66 includes a front side 138 and a rear side 140. The front (outer facing) side 138 of the PCBA includes a light ring, generally designated 141 and represented, for example, by a series of exemplary LEDs 142a-d, spaced circumferentially around the disc 66. In this exemplary embodiment, there are twenty-four such LEDs shown in FIG. 12 (although not all labeled) that together define the LED ring 141 aligned with the internal LED diffuser surface 96 of the front piece 60 of the primary housing 34 when assembled. It will be appreciated that more or fewer LEDs may be used to define the ring or that even a single isolated or ring shaped LED may be used. In addition, the spacing between adjacent LEDs may be varied to alter the light characteristics emitted through the front piece 60. In addition, one or more light emitting sources may be disposed on the rear side 140 to emit light rearwardly toward the user or positioned to direct light radially outwardly through a corresponding window or translucent or transparent section of the housing 34 as well.

With particular reference to FIG. 13, the rear (inner facing) side 140 of the PCBA includes a number of additional functional circuits or components contributing to the functionality of the modular breath tracking and training system 30. At the twelve o'clock position on the disc 66, a communication device 144 is mounted to the PCB 66. Communication device 144 is operable to at least transmit data and also preferably to receive data as well allowing the system 30 to communicate either in one direction or both directions with external devices and may be constructed to communicate using a wireless communication protocol such as that offered over cellular, wireless, Bluetooth, near field communications network. By employing a communication device, the system 30 is capable of providing real-time remote monitoring of the respiratory data captured by the one or more sensors allowing for immediate analysis and feedback as well as interactive feedback generated by a remote device having a user-friendly app (software program) that displays real-time breathing patterns, progress reports and guided training sessions while encouraging user engagement and adherence.

With continued reference to FIG. 13, at approximately the two o'clock position a haptic sensor with a motor 146 and a rumbler 148 is provided for haptic feedback purposes. At the three o'clock position a USB connector port 150 is provided to receive a USB connector for charging the rechargeable battery 68. Alternatively, the USB connector may be used to retrieve or send data to the PCBA 64. At approximately the four o'clock position, a battery plug 152, harness connector, or contact surface is provided for connecting the battery 68 to the PCBA 64 as the power source. Moving clockwise around the disc 66 to the six o'clock position is a flat space 154 for receiving one end of the battery 68. At approximately the eight o'clock position an accelerometer 156 is provided to detect the orientation of the modular breath tracking and training system 30. The accelerometer may also be used to detect whether the device has moved and should power on or has not moved in a certain time period and should be turned off. In between the eight and nine o'clock positions is an onboard microprocessing unit 158. Such microprocessing unit may be a simple counter for counting fan rotations as well as calculating rotation rate and determining fan direction that are then sent to a remote device for further processing as described below or a more sophisticated programmable processing device with sufficient functionality and storage capacity to allow the modular breath tracking and training device to be used a standalone device by processing a multitude of parameters and calculating outcomes using pre-programmed formulas on board the PCBA 64 along with sufficient storage to retain at least some of the data. At the nine o'clock position on the disc 66, a power button 160 is provided as a means for turning the system 30 on and off. When the system is assembled, the power button 160 is covered by a flexible push button cover 124 (FIGS. 1-4 and FIGS. 6-9) that seals off that opening and assists in protecting the interior components from the elements. At approximately the ten o'clock position a speaker unit 162 is provided to provide audible feedback during use.

With continued reference to FIG. 13, positioned around the orientation tooth 134 and facing toward the central opening 136 of the disc 66, is a counterclockwise optical sensor 164 and a clockwise optical sensor 166 positioned to either side of a centrally located (twelve o'clock position) light source 168. This trio of components (164, 166, and 168) are used to detect the initial direction and rate of rotation of the fan within the turbine sub-assembly 36 as well as described below. The light source 168 is preferably an infrared emitter but this is not meant to be limiting. In addition to the electronic components positioned around the rear side 140 of the PCB 66, a set of four spaced apart holes 170a-d are positioned about the interior perimeter 132 of the PCB 66 allowing the threaded fasteners that couple the rear section 62 to the front section 60 of the primary housing 34 together to pass through the PCB 66.

When the primary housing 34 is assembled as shown in FIGS. 1-9, the PCBA is enclosed by the outermost section 60 and the innermost section 62 when secured together by elongated threaded fasteners (not shown) passing through openings 172a, 172b, for example, in the rear wall 106 (FIG. 4), through the guide posts 118a-d, through the holes 170a-d in the disc 66, and into the threaded posts 94a-d of the front piece 60 of the primary housing 34. The assembled outmost section 60 and innermost section 62 cooperate to protect the PCBA from the elements. The threaded fasteners passing through the holes 170a-d in the PCB also fix the PCB 66 in place within the primary housing 34 with the disc sandwiched between the guideposts 118a-d and threaded posts 94a-d. It will be appreciated that the innermost section 62 and outermost section 60 may be snapped or clipped together, welded, or otherwise suitably joined as an alternative to using threaded fasteners. Seals along the joint lines between components may be introduced for additional protection against the elements. The joining of the outermost section 60 and innermost section 62 forms a shell around the PCBA 64 while leaving a central passage therethrough and a recessed seat for the interactive airway chamber 36. The leading edge 104 of the innermost section 62 matches a trailing edge 174 (FIG. 10) of the outermost section 60 in diameter. When the outermost section 60 and innermost section 62 of the primary housing 34 are coupled together, the complementary portions 100, 122 on the left hand side (FIG. 5) define a cavity to receive the USB connector port 150 (FIG. 13) while complementary portions 98, 120 on the right hand side (FIG. 6) leave a cavity for a power button 160 (FIG. 13).

Turning now to FIGS. 9, 14, and 15A-D, the interactive airway chamber 36 is provided in the form of a turbine sub-assembly that may be plugged into the primary housing 34 in this exemplary embodiment. More specifically, the turbine sub-assembly includes a front cover 180, a fan element 182, a rear cover 184, and an optional spit screen or guard 186. In this exemplary embodiment, the front cover includes a series of spokes 188a-c projecting from a central outer hub 190 to an outer ring 192. The spacing of the spokes defines a series of adjacent openings 194a-c allowing for bi-directional airflow. A sidewall 196 projecting rearwardly from the outer ring 192 includes a boss 198 for releasably locking the front cover to the rear cover when assembled together. The interior surface (not shown) of the hub 190 includes a recess for receiving one end of an axle stub 204 projecting from or passing through the fan element 182.

Figure 14:
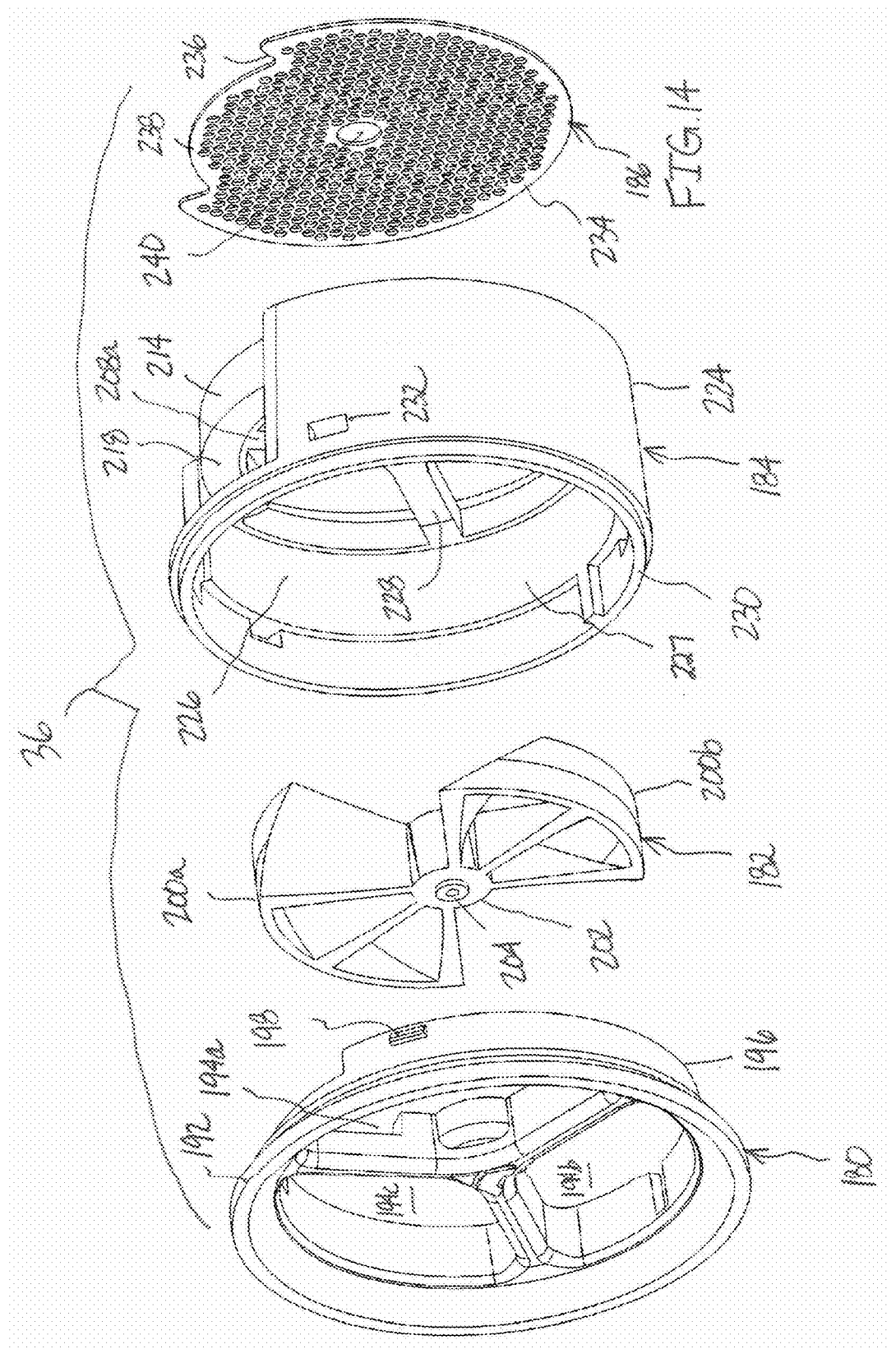
FIG. 14 is an exploded perspective view of an exemplary turbine sub-assembly from FIG. 9, in enlarged scale.
Figure 15:
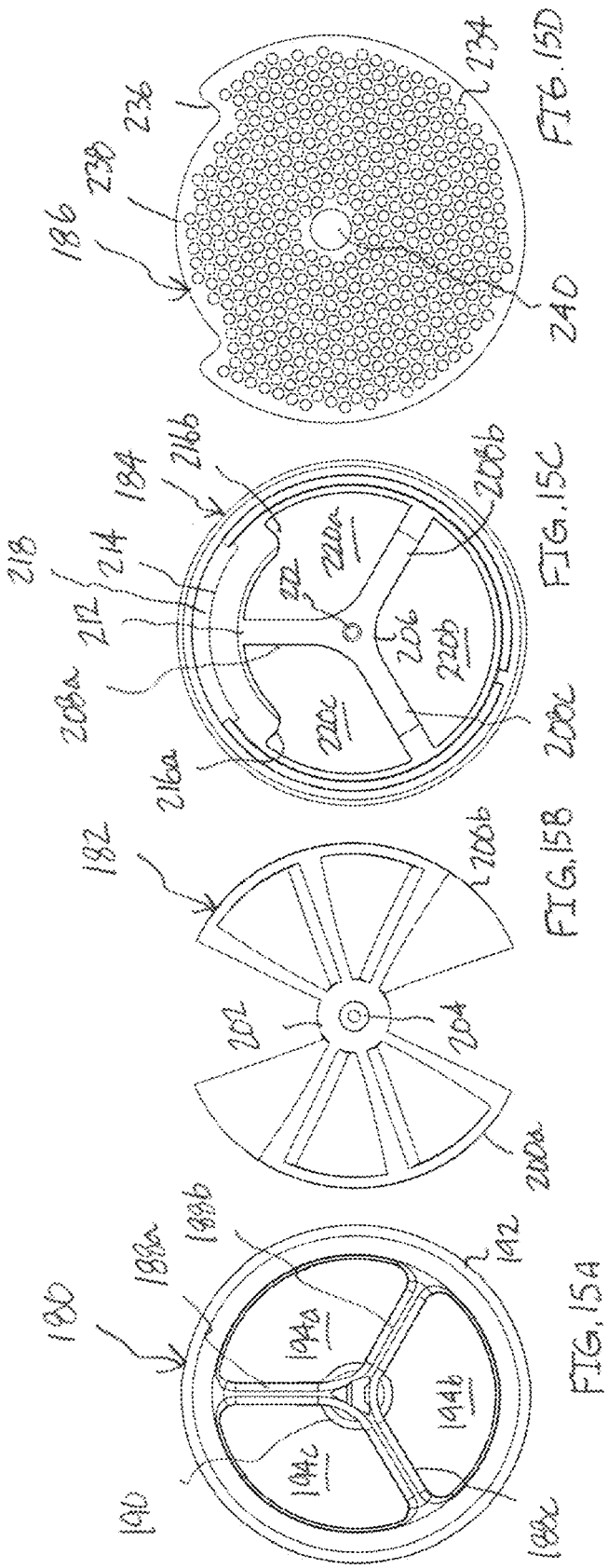
FIG. 15A-D are front orthographic views of the turbine sub-assembly components of FIG. 14, in reduced scale.

With continued reference to FIGS. 14 and 15B, the fan element 182 is a bi-directional bat-wing shaped fan including diametrically opposed blades 200a, 200b projecting outwardly from a central fan hub 202 which may contain a central bore for receiving an axle or, as shown in FIG. 14, an axle stub 204 for rotational coupling to the interior surface of the hub 190 of the front cover 180. A similar rear stub (not shown) projects from the rear surface of the fan element 182. The fan is rotationally responsive to both inhalation airflow and exhalation airflow which drive the rotational direction of the fan relative to the fixed spokes 188a-c of the front cover 180. It is preferable to minimize any friction associated with the rotation of the fan element. Thus, a suitable lubricant, support bearings or sleeves, friction reducing materials, or other suitable rotational coupling may be used. Alternatively, the fan may be magnetically suspended with the turbine sub-assembly to diminish any frictional resistance. In other embodiments, however, the frictional resistance may be increased to implement a different training regimen.

The rear cover 184 somewhat resembles the front cover 180 but includes a smaller in diameter fan support hub 206 with three projecting spokes 208a-c projecting therefrom to an outer ring 210. The outermost end 212 of the upwardly projecting spoke 208a terminates interior to the outer ring 210 and joins a circumferentially projecting segment 214 that turns outwardly at its outermost opposing ends 216a, 216b to join back to the outer ring. Such construction defines an optical passthrough window 218 best seen in FIGS. 14 and 16-17 that is constructed to aid the optical sensors in detecting fan blade movement as described below. As with the front cover 180, the rear cover also includes a series of spaced apart openings 220a-c between adjacent spokes 208a-c. The support hub 206 includes a recess 222 for receiving an axle stub or boss (not shown) projecting from the rear surface of the fan element 182. The rear cover includes an elongated sidewall 224 (FIG. 14) with the spokes 208a-c positioned at the innermost extent of the sidewall to define a forward facing recess 226. The depth of the recess between the front surface 228 of the spokes 208a-c and forward most perimetrical edge 230 and diameter of the recess provides space for the fan element 182 and the sidewall 196 of the front cover to fit therein with the fan element being free to rotate on its axle or axle stubs therein. The sidewall 224 of the rear cover piece 184 includes a slot 232 for releasably receiving the boss 198 of the front cover 180 to assist in releasably locking the front cover 180 and the rear cover 184 together. When assembled, the outer ring 192 of the front cover 180 abuts the peripheral edge 230 of the rear cover 184 and the two components 180, 184 define a removable secondary housing unit that contains the fan element 182.

Still referring to FIGS. 14 and 15D, an optional component that may be incorporated into the turbine sub-assembly 36 is the spit screen or spit guard 186 is a relatively thin disc with a perforated area 234 including a plurality of small diameter openings to reduce the likelihood of a user's spit or spray from contacting and interfering with the rotational speed of the fan element 182. The holes may further be covered with a thin filter layer to further reduce the likelihood of spit passing therethrough to impact the fan. The upper end of the spit guard includes a notch 236 with an outermost edge 238 constructed to align with the outer edge of the circumferentially projecting segment 214 without obstructing the window 218 allowing the optical sensors to detect the fan blade movement in use. A central hole 240 is used to secure and orient the spit guard on the back surface of the rear cover 184. It will be appreciated that the spit guard 186 may be removed completely to define a minimum resistance profile (i.e., little to no airflow resistance) or the holes in the perforated area 234 may be practically sealed off to define an alternative resistance profile with a maximum or near maximum resistance. In addition, the holes in the perforated area may be varied to define other alternative resistance profiles of the airflow passing therethrough between the maximum and minimum resistance profiles.

Figure 16:
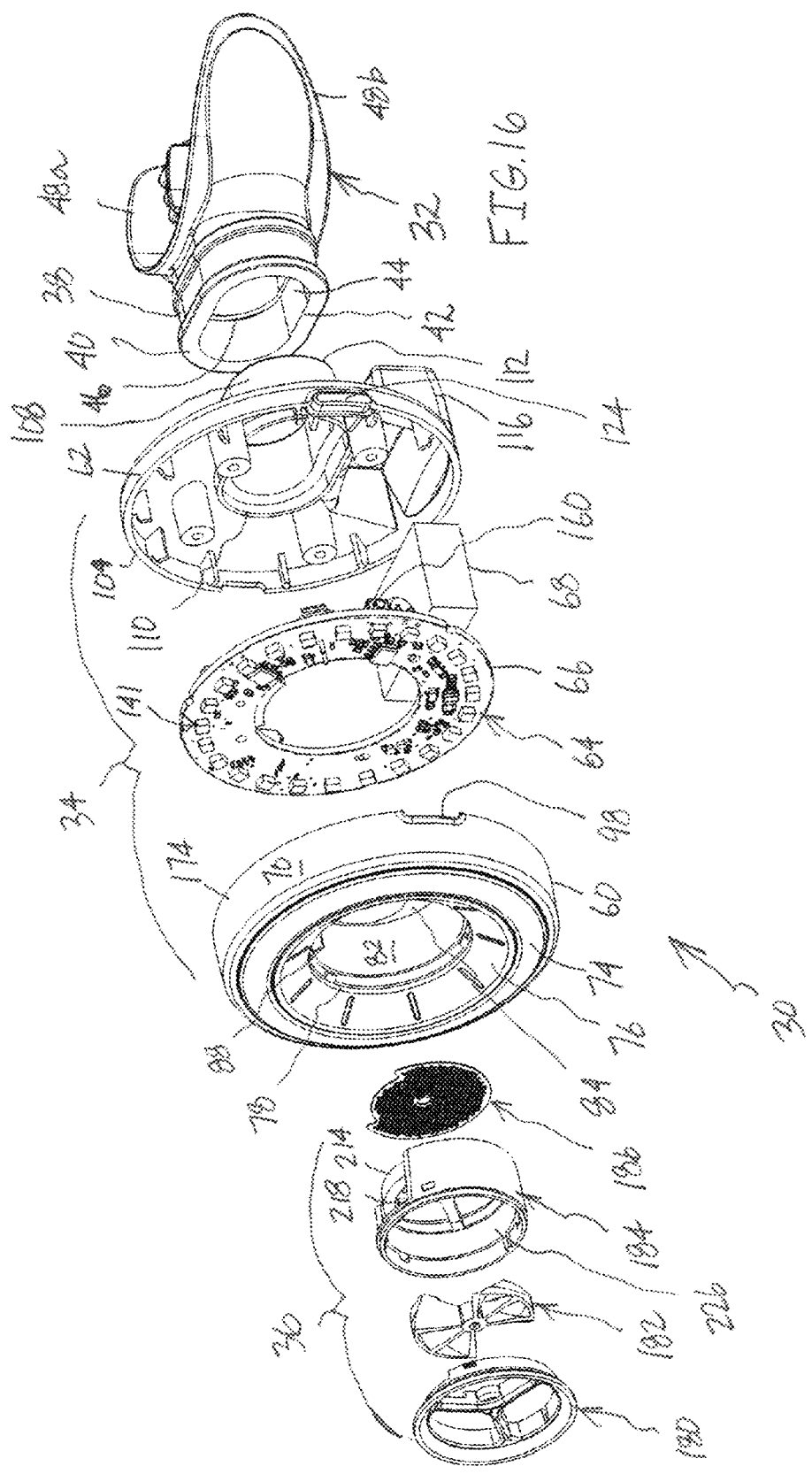
FIG. 16 is an exploded perspective view of the sub-assemblies and mouthpiece from FIG. 9, in reduced scale.

Turning now FIGS. 9 and 16, the assembly and airflow through the modular breath tracking and training system 30 will now be described. As shown in FIG. 16 with the components of the system 30 completely disassembled, the fan element 182 may be disposed within the recess 226 of the rear cover piece 184 and then the front cover piece 180 inserted into and snapped together with the rear cover piece to rotationally sandwich the fan therebetween. In this configuration, the spokes 188a-c of the front cover 180 radially align with the spokes 208a-c of the rear cover which in turn aligns the openings 194a-c of the front cover with the openings 220a-c of the rear cover piece. The notch 236 of the spit guard 186 may then be aligned below the window 218 of the rear cover piece and placed in an abutting relationship with the interior surface of the rear cover piece. The central hole 240 of the spit guard also assists in aligning the spit guard so as not to block the window 218. At this point, the turbine sub-assembly 36 resembles the configuration shown in FIG. 9. It will be appreciated that the airflow path through the turbine sub-assembly may have straight cylindrical walls, include a narrow throat section to establish a venturi effect, or including an expanding throat section to vary the airflow passing through the turbine sub-assembly 34.

With continued reference to FIG. 16, the battery 68 may be inserted into the battery receiving compartment 116 of the rear housing 62. The battery may be connected to the battery plug 152 on the rear surface 140 of the PCBA 64. The holes 170a-d of the PCB disc 66 may be aligned with the fastener guide posts 118a-d of the rear housing 62 with the power button 160 aligned at the three o'clock position (as viewed in FIG. 16) and the USB connector 150 aligned at the nine o'clock position. The front housing 60 may then be aligned with the rear housing 62 to dispose the power button slot 98 and the USB connector slot 100 in alignment with their respective counterparts 120, 122 on the rear housing. Threaded fasteners (not shown) may be inserted through the holes in the rear wall 106 of the rear housing 62, through the guide posts 118a-d, through the corresponding holes 170a-d, and threaded into the threaded fastener receiving posts 94a-d to secured the front housing 60 to the rear housing 62 with the PCBA 64 sandwiched therein and the battery 68 disposed therein as well and connected to the PCBA. The push button cover 124 may be press fit into the push button slot to cover the push button 160 or inserted during assembly of the front and rear sections 60 and 62. At this point, the primary housing sub-assembly 34 resembles the configuration shown in FIG. 9.

Figure 17:
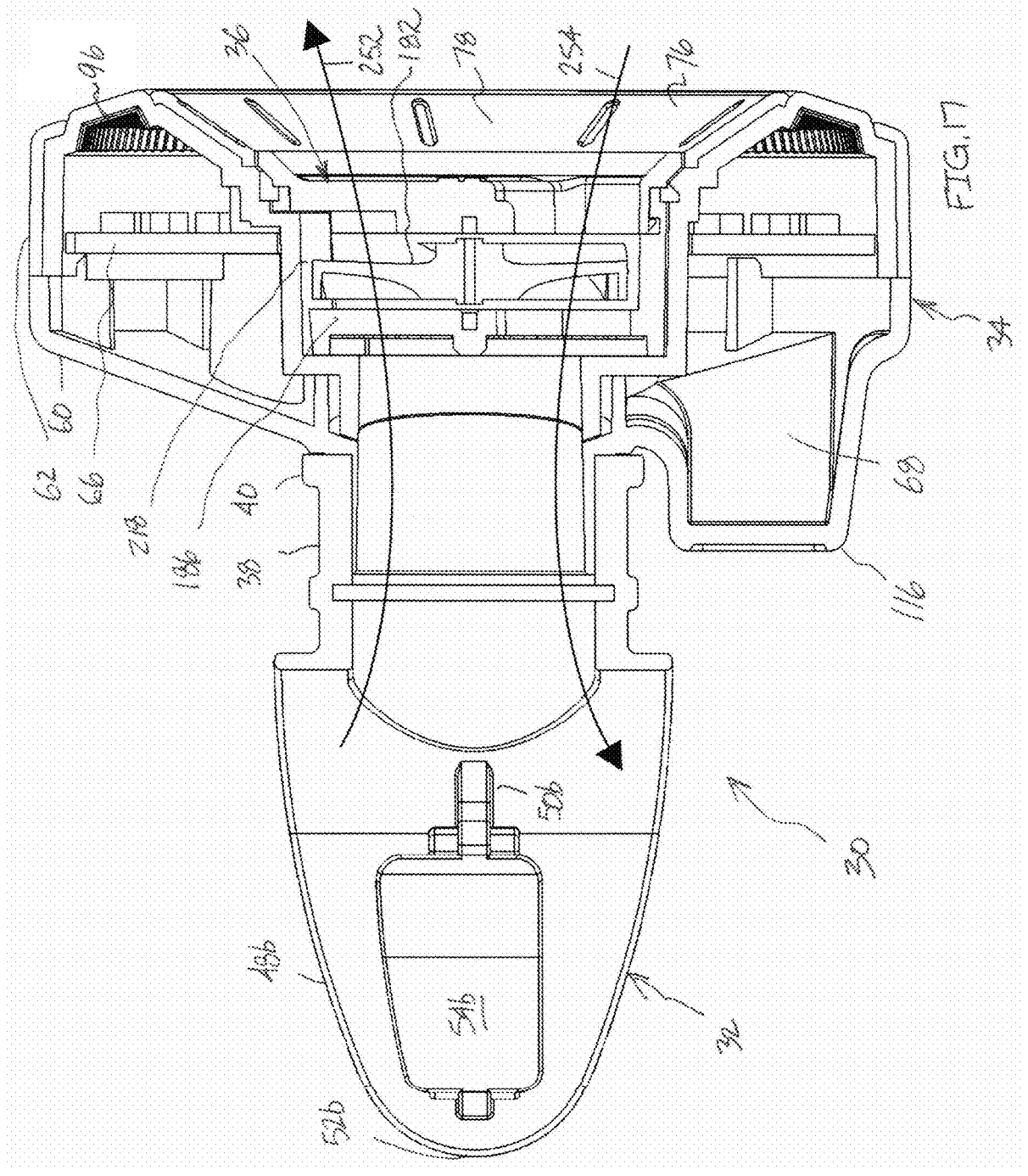
FIG. 17 is a cross-sectional view taken through a central plane of an exemplary assembled modular breath tracking and training system of FIG. 5, in enlarged scale.

The turbine sub-assembly 36 may then be slip fit through the central opening 78 of the assembled housing 34 and into the turbine (or plug) receiving recess 80 with the innermost extent of the sidewall 224 of the rear cover 184 abutting the interior surface of the turbine sub-assembly receiving seat 84 and the sidewall 224 also abutting the internal sidewall 227 (FIG. 14) of the recess 226. The arched section 88 assists in orienting the turbine sub-assembly within the recess 80. This ensures that the window 218 in the rear cover piece 184 of the turbine sub-assembly remains clear and unobstructed. The turbine sub-assembly is essentially plugged into the primary housing and resembles the assembled configuration 250 shown in FIG. 18 at this point. In this configuration, the plug receiving recess 80 and the interactive airway chamber 36 are preferably co-axially aligned in this exemplary embodiment. However, this is not meant to be limiting, and the central axes passing through the plug receiving recess and the interactive airway chamber may also be offset to one another. Also, in this configuration, the turbine assembly 36 is positioned such the fan element 182 is positioned within the central opening 136 of the PCB disc 66 wherein the light source 168 shines light radially downwardly on the fan blades 200*a*, 200*b* which are exposed to the light source through the window 218 as the fan element 182 rotates. This is best shown in FIG. 17, a cross-sectional view of the turbine sub-assembly 36 fully plugged into the primary housing 34.

Figure 18:
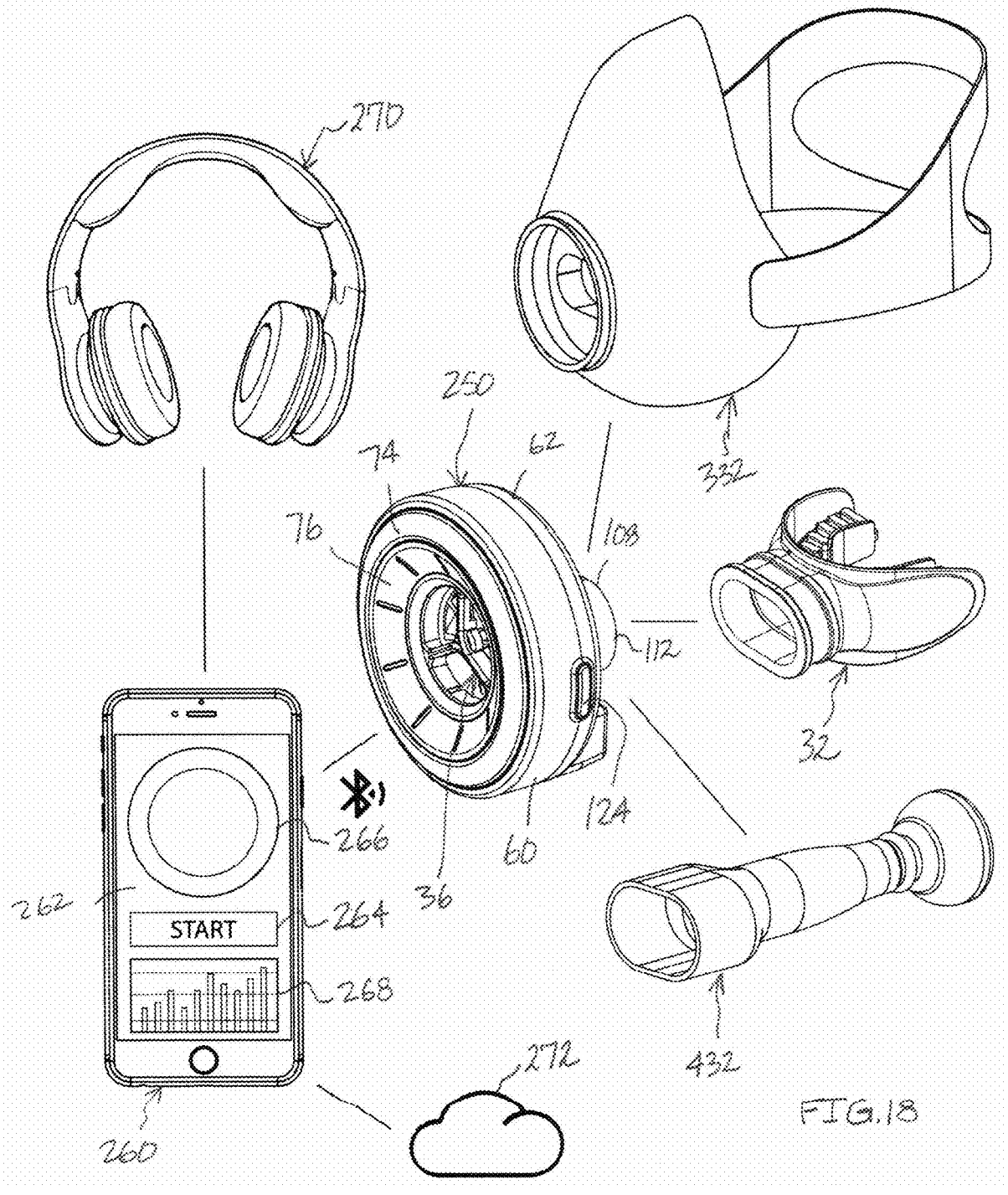
FIG. 18 is a schematic depicting a variety of exemplary components that may be used with the modular breath tracking and training system.
Figure 19:
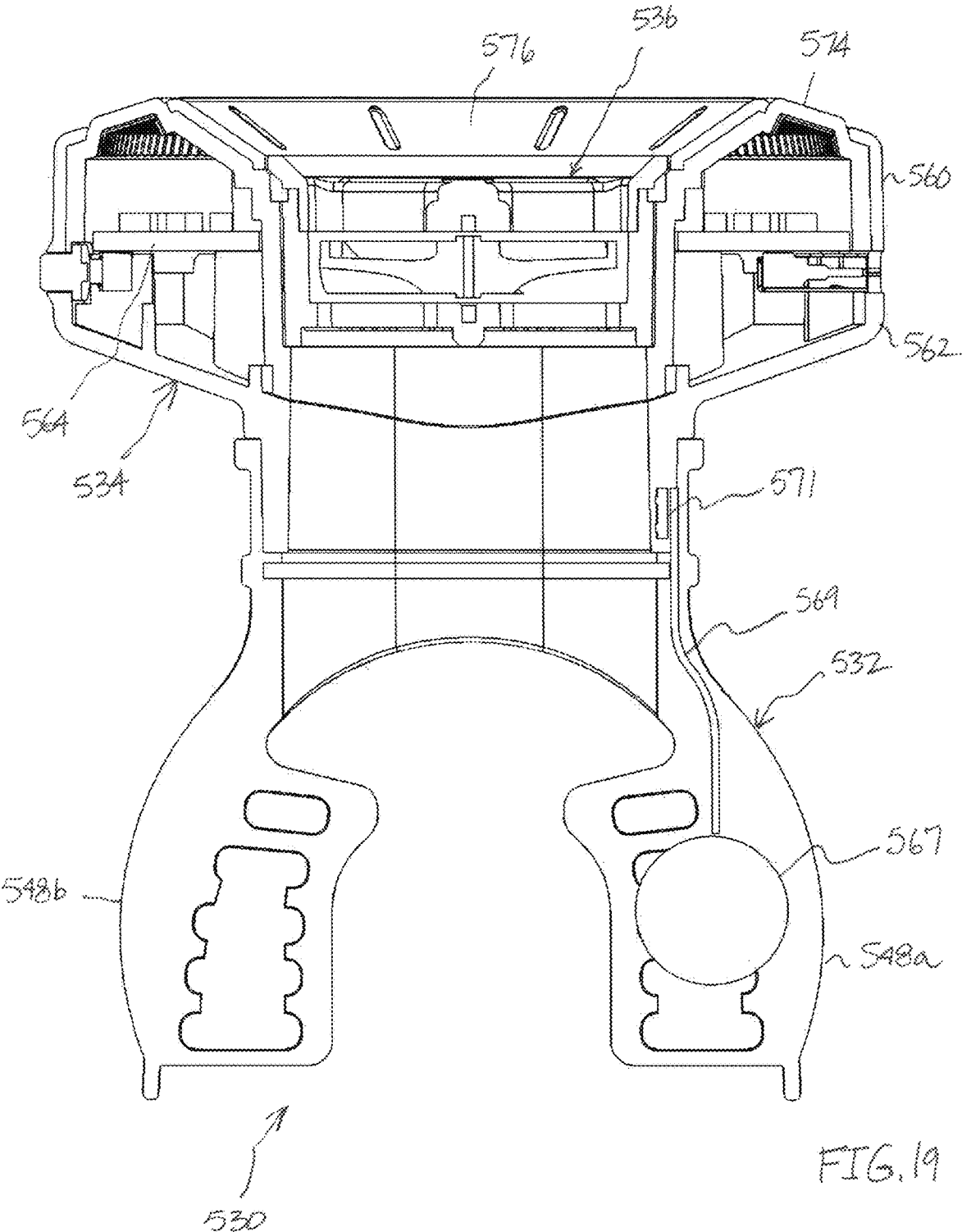
FIG. 19 is a top cross-sectional view taken through a central plane of an alternative embodiment of a modular breath tracking and training system incorporating an alternative sensor location.

With the turbine sub-assembly 36 plugged into the primary housing 34 as shown in FIG. 19, the assembly 250 (FIG. 18) may be releasably secured to the respiratory orifice interface 32. In this primary embodiment the interface 32 is a mouthpiece. The racetrack shaped mounting section 38 of the mouthpiece 32 is friction fit over the complementary shaped racetrack shaped tube 108 of the rear section 62 of the primary housing 34 until the enlarged flange 40 abuts or is moved proximate to the rear wall 106. At this point, the configuration of the system 30 resembles that shown in FIGS. 1-8 and the system 30 is ready for use.

Turning now to FIG. 18, it will be appreciated that the design of the embodiments of the modular breath tracking and training system 30 allows for interaction with a variety of devices. For example, the primary housing 34 and interactive airway chamber 36 installed therein and collectively designated 250 may be disengaged from the mouthpiece 32 and inserted into a mask 332 or a musical instrument mouthpiece 432, such as that used on a trumpet or other wind instrument. In the case of the mask, both the nasal and oral orifices may be covered. Thus, the user may selectively choose which orifice to breath out of and interact with the assembly 250. In addition, the mask may include a septum or divider effectively isolating the nasal orifice of the user from the oral orifice of the user for a different experience with the assembly 250. An adapter piece may be used between the respective components to merge the various respiratory orifice interfaces 32, 332, 432 and the assembly 250 if necessary. As an alternative to a mask, hollow nasal clips inserted into a user's nasal orifices and coupled directly to the assembly 250 may be used to measure airflow passing through the user's nasal orifices. On the other hand, nasal clips of the variety that seal off a user's nose may be used in conjunction with a mouthpiece to ensure all breathwork is only directed therethrough. Such examples of the various fitments (mouthpiece, masks, nasal clips, musical mouthpieces) are not meant to be limiting and other such interfaces and fitments may be used with the assembly 250.

With continued reference to FIG. 18, in addition to having a modular capability to releasably interact with various respiratory orifice interfaces, the assembly 250 may also communicate with one or more mobile devices to extend the processing power of the modular breath tracking and training system 30 and add additional interactive options. For example, the communication device 144 on the PCBA 64 (FIG. 13) enables the system to communicate with a mobile device 260 through a cellular, wireless, Bluetooth, or near field communication protocols. The mobile device may receive sensor data from the communication device 144 and process according to software programs and algorithms stored therein and executable thereon. The coding of such programs may be human, AI driven, or a combination thereof. The mobile device preferably includes a user interface 262 with one or more display sections. In this exemplary embodiment, the user interface 262 includes a text prompt section 264, a ring shaped display indicator 266 synchronized to the light ring 141, and a statistics section 268 wherein the user may review their past and present breathwork statistics as well as future goals. Extending the system 30 capabilities further, the mobile device 260 may be placed in communication with a headset 270 or ear buds, either through a direct wired connection or a wireless connection for additional audio experiences, feedback, and/ or guidance. The mobile device 260 may be also be placed in communication with a local or large scale network 272 as would readily be understood by one of ordinary skill in the art. Such communication allows for access to larger storage capacity and access to apps or other programs that may be used with the system 30. While a mobile device is referenced in this example and would include mobile phones, smartphones, laptops, tablets, watches, wearables, smart glasses, virtual reality and augmented reality devices, and other portable devices capable of communicating with the system 30, a desktop computer, workstation, or other less portable devices may be placed in communication with the system 30 as well and used to provide the same or similar functionality.

Materials used: The mouthpiece is preferably constructed of food-grade elastic material, high-purity silicone, soft and comfortable, retractable material. The PCBA may be constructed using surface mount technology (SMT) or thru-hole technology (THT). Most of the other components are constructed from a rigid plastic material and may be constructed using conventional manufacturing methods. The fan is preferably constructed of a metallic material, metal alloy, a plastic material, or other suitable material, and may include a reflective element. A suitable communication and sensor processing device 144 and/or 158 has been found to be an Apollo3 low power System on a Chip (SOC) model available from Ambiq. A suitable optical LED 168 has been found to be an infrared emitter model No. SFH 4045N available from ams-OSRAM USA INC. A suitable optical detector 164, 166 has been found to be a phototransistor model No. 1541021NCA170 available from Würth Elektronik. A suitable buzzer/speaker 162 for providing the audio feedback and/or prompting has been found to be a buzzer piezo model no. PKLCS1212E2000-R1 available from Murata Electronics. A suitable haptic sensor 146, 148 for providing vibration based feedback and/or prompting has been found to be a vibration motor model No. VZ6DCBB0735091 available from Vybronics Inc.

While chips and other PCBA 64 devices may be provided individually, such items may also provided in integrated packages such as those available in System on a Chip (SOC)

or System on Module (SOM) options that provide the core components of an embedded processing system—including processor cores, communication interfaces, and memory blocks. Another solution is to provide an onboard chip capable of handling artificial intelligence functionality. Once such solution has been found to the low power Neurosense AI chip, Product Name Neurosense NS150-01 and NS150-02, commonly used in wearables. The Neurosense chip is constructed to measure heart rate measurements and other sensor raw data. Other microcontroller units (MCUs), chips, modules, or systems on a chip capable of integrating with edge AI may be suitable as well. Such devices are preferably located within or on the modular breath tracking and training system 30 to provide onboard AI capabilities and AI based computations where the data is collected by the sensors and fed to the AI program thus omitting the need for cloud based connectivity and further supporting the system 30 as a standalone AI capable device, although cloud connectivity may still prove beneficial. Such materials described herein are merely preferred suggestions and other suitable materials will occur to one of ordinary skill in the art.

Use of the Modular Breath Tracking and Training System: In use, an applicable respiratory orifice interface 32, 332, 432 is selected for use with the turbine and primary housing assembly 250, assumed to be assembled in this example. In this example, the selected respiratory orifice interface is the mouthpiece as shown in FIGS. 1-9 and 16-18. The mounting section 38 of the mouthpiece 32 is inserted onto the tubular extension 108 of the rear section 62 of the primary housing 34 and slid along until the enlarged flange 40 practically abuts or is placed proximate the rear wall 106 of the rear section 62 of the primary housing thus completing the assembly of the modular breath tracking and training system 30. At this point, the assembled system 30 resembles the configurations shown in FIGS. 1-8 for example.

The user may then insert the mouthpiece 32 into their mouth to position the bite grips 50a, 50b between their upper and lower sets of teeth and the bite wings positioned along their cheeks to provide a sufficient seal. This action is similar to using a scuba diving mouthpiece and would be familiar to one of ordinary skill in the art. With the mouthpiece positioned in place, the user may depress the power button 160 (FIG. 13) to turn the system 30 on. Alternatively, merely picking up the system 30 may be sufficient to trigger the accelerometer 156 (FIG. 13) to detect movement and turn the system on as well. The LED ring, generally designated 141 and including representative LEDs 142a-d in FIG. 12, for example, may illuminate with a particular color and/or intensity to indicate the system is on and activated. Alternatively, the power button may illuminate to indicate an on/active status that also turns on the light source 168 on the PCBA 64 (FIG. 13). With the device 30 in a ready state, the user may simply perform one or more breathwork exercises, either on their own program or as guided by one or more onboard feedback or guidance devices 141, 142a-d, 146/ 148, 156, 162, for example, or the user interface 262 on a connected mobile device 260. More specifically, the user may simply exhale into the mouthpiece 32 which captures the airflow created by the exhalation and funnels the airflow from the user's mouth through the respiratory side opening 46, through the airflow transfer channel 44 and out the distal opening 42 of the mouthpiece 32 to enter the proximal opening 112 of the racetrack shaped tube 108 of the rear housing 62 of the primary housing 34. Under continued exhalation force, the exhaled airflow continues out through the distal opening 110 of the tube 108 and through the central opening 78 of disc 66 to pass through the perforated area 234 in the spit guard and through the spaces 220a-c between the spokes 208a-c of the rear cover 184. After passing through the spaces 220a-c, the airflow encounters the fan element 182 or turbine. The movement of the exhaled airflow across the fan blades 200a, 200b causes the fan to turn in a particular direction. The initial movement of the fan blades trips one of the optical sensors 164 or 166 first by blocking the light source 168 through the window 218 of the rear cover piece 184. Based on the first tripped optical sensor, the direction of the fan is determined, either clockwise or counterclockwise. A signal is transmitted from the tripped optical sensor to the microprocessor 158 (FIG. 13) and a direction is determined. At this point, the system 30 detects whether an exhalation or inhalation is taking place. As the fan 182 continues to rotate during the exhalation process, the rate of rotation may also be determined as the fan blades pass across and are detected by the optical sensors 164, 166. The rate of rotation signal is fed to the microprocessor 158 which may calculate the airflow rate passing through the fan and turbine sub-assembly 36. Airflow continues out through the turbine sub-assembly 36 and out through the spaces 194a-c between the spokes 188a-c of the front cover piece 180 and on out through central opening 78 of the front piece 60 of the housing 34, During this process, the light ring 142a-d may illuminate with a brightness proportional to the fan speed to indicate the strength or weakness of the exhalation. The inhalation process is similar except that the fan direction changes and rotates in the opposite direction and the airflow is drawn in through the central opening 78 and traverses the reverse path and into the user's lungs through the mouthpiece 32. The light ring may also illuminate with a different color to provide a visual indicator corresponding to the direction of the airflow. Exemplary airflow paths for exhalation 252 and inhalation 254 are shown in FIG. 17. It is worth noting that the exhalation path 252 and inhalation path 254 both transverse through common ports and common chambers as a dedicated inhalation path separated from a dedicated exhalation path is unnecessary in this exemplary embodiment. The user may repeat the process of exhaling only by breathing in through their uncovered nose and out through their mouth into the system 30, inhaling only by breathing out through their nose and in through their mouth, or alternating between inhaling and exhaling through the device only through their mouth. Other exemplary breathwork examples include a deep inhalation followed by expelling as much from the lungs as possible or vice versa, breathing in and out in rapid succession, breathing in a box pattern, inhaling and holding, breathing in a particular pattern while conducting some other movement such as exercise, and inhaling and exhaling over different time periods. Other breathwork examples will occur to those familiar with breathwork training and all may be monitored and guided by the system 30. As explained above, once the device 30 reaches the ready state, the user may simply perform one or more breathwork exercises, either on their own program or as guided by one or more onboard feedback or guidance devices. Thus, all breathwork and training exercises may be conducted completely hands-free as there is no need to maintain the user's hand or hands n the primary housing 34 or the mouthpiece 32 once the device is in the ready state since the user may support the entire system 30 solely by capturing the mouthpiece 32 as explained above. The same hands-free use is true for the coaching and prompting features as the system 30 such as those offered by the light ring as explained above as well.

While using the modular breath tracking and training system 30, a variety of feedback and training components may be implemented to track and/or train or coach the user. For example, one or more LEDs 142*a-d* in the light ring 141 (FIG. 12) may illuminate to a particular rhythm or timing to train the user to follow and perform breathwork accordingly. In addition, one or more LEDs may change color to guide the user as well. The haptic device 146, 148 (FIG. 13) may vibrate according to a designated rhythm or timing to also instruct or guide the user in performing their breathwork exercises. Similarly, the speaker unit 162 (FIG. 13) may emit audible beeps or other sounds to provide a breathwork guide for the user to follow. Any of the feedback devices, whether visual, audible, or haptic may be used to both provide a targeted rhythm or timing to follow or notify the user if the breathwork is off track or not keeping up with the sensory prompts. In addition, one or more feedback and prompting devices 141, 142*a-d*, 146, 148, and/or 162 may used alone or in conjunction with one another. For example, the LED ring 142*a-d* may illuminate during an exhalation and the speaker device beeps when the cycle is complete.

The prior use descriptions illustrate the functionality of the modular breath tracking and training system 30 primarily as a standalone device. However, the system 30 may be used in conjunction with one or remote tools as well. For example, communication device 144 (FIG. 13) may pair or otherwise communicate with a mobile device 260 (FIG. 18) using conventional communication protocols. While additional processing power may be brought on board the PCBA 64 as well as additional storage capacity and programming modules stored therein, it may also be efficient to pair the modular breath tracking and training system 30 with a more powerful processing device 260 with a user interface 262. With the system 30 connected to the mobile device 260, the user may follow one or more text prompts from the text prompt section 264 or follow the visual light ring 266 that may be synchronized with the light ring 141, and also view their statistics, both past and present, as well as their future goals in the stats section 268. The mobile device may be programmed with or include apps that provide breathwork training exercises to expand the functionality of the standalone system 30.

By determining this information detected by the optical sensors 164, 166, a determination of whether the airflow is an inhalation or an exhalation may be made. In addition to the direction of the airflow, the speed of the fan blades may be determined by how rapidly the blades repeatedly trip at least one of the optical sensors. The fan and optical sensors essentially operate as an anemometer by measuring airflow characteristics including at least one of wind speed, direction, and velocity while other suitable sensors may be incorporated into the PCBA 64 to measure other characteristics such as temperature, pressure, and oxygen consumption sensors such as heart rate sensors for measuring VO2 max (maximal oxygen consumption) or VO2 (peak oxygen consumption). As another example, a pressure sensor may also be mounted anywhere in the airflow path within the respiratory orifice interface 32, the primary housing 34, and/or the interactive airflow chamber 36 of the system 30 to detect pressure resulting from exhalation or inhalation breathwork. Another alternative embodiment swaps out the optical sensors and light source for a Hall effect sensor wherein a pair of magnets with opposing poles are mounted on the fan blades or fan axle and during rotation pass by a Hall effect sensor to detect fan direction and rotational speed. From the foregoing, it will be appreciated that the modular breath tracking and training system 30 may utilize a variety of flow sensors, humidity sensors, and pressure sensors alone or in combination to gather comprehensive respiratory data. These sensors may be calibrated to detect subtle variations in breathing, ensuring high accuracy and reliability.

In addition, the light ring 141 is responsive to either the airflow sensed passing through the primary housing 34 or signals transmitted from the electronic processing device 64 or both. The light ring may be used as both a feedback indicator responsive to the user's breathing patterns passing through the primary housing 34 or, alternatively, as a prompting device for instructing the user how to perform breathing exercises.

The accompanying software platform, whether on-board the system 30 or stored in a remote device 260 (FIG. 18) processes the captured data using respiratory calculation related algorithms to assess breathing quality and breathing patterns and further identify areas for improvement. In addition to the on-board prompts provided by the haptic, light, speaker, and accelerometer devices mounted on the PCBA 64, users can access personalized training programs through a mobile app, which offers interactive exercises, visual cues, and auditory feedback to guide users through their training sessions. For example, the modular breath tracking and training system 30 may be used for athletic training by enhancing endurance and performance through targeted breathing exercises, for stress management by offering guided breathing routines to promote relaxation and reduce anxiety, for respiratory rehabilitation by supporting recovery and strengthening of lung function post-illness or surgery, and/or sleep improvement through monitoring and improving breathing patterns for better sleep quality. Such exemplary cases are not meant to be limiting.

Referring now to FIG. 19, an alternative embodiment of the modular breath tracking and training system, generally designated 530, is depicted. As much of the construction in this exemplary is the same as earlier embodiments, like components are like numbered. For example, the alternative embodiment 530 includes a respiratory orifice interface 532, a primary housing 534, and an interactive airflow chamber 536. The respiratory orifice interface 532 includes bite wings 548*a*, 548*b*. The primary housing includes a front section 560 and a rear section 562, the front section including an outer light ring cover 574 and inner ring funneling section 576. The primary housing covers and protects a PCBA 564. The primary alteration in this embodiment is the incorporation of a heart rate sensor 567 disposed at an alternate location relative to the PCBA and instead located within the right side bite grip 548*a*. The heart rate sensor 567 may be coupled to the PCBA 564 via a wiring harness 569 or other electrical signal transmission line running through the bite grip 548*a* to a PCBA connector 571. The heart rate sensor 567 is constructed to receive vibrations emanating from the user's teeth while gripping either one or both bite grips and convert the vibrations into a heart rate signal to provide yet another measured parameter to the microprocessor 158 for calculating a user's heart rate during use. A suitable sensor may be provided in the form of a piezo electric sensor constructed to measure changes in pressure, acceleration, temperature, strain, or force by converting them to an electrical charge or directly proportional voltage. Such device may be tuned to the user's specific vibrations or tailored to differentiate a particular vibration from the heart rate vibration to isolate the signal of interest. One suitable piezo electric sensor has been found to be model No. AB1541 available from PUI Audio, Inc.

Other energy harvesting systems may also be incorporated into the system 30. As another non-limiting example, the kinetic energy created by the user's own breathwork resulting in the fan rotation may be converted to generate sufficient power to power one or more components of the PCBA 64 and other electronic components of the system 30.

In addition to the foregoing, it will be appreciated that the turbine sub-assembly 36 may be removed as well and exchanged with different turbine sub-assemblies or plugs, including those having alternative airflow interactive triggers. It will also be appreciated that the sensors in the primary housing may be moved to the turbine sub-assembly. The turbine sub-assembly and primary housing may also be constructed as an integral unit, although the modularity is preferred since the modular nature of the system allows for easy customization, maintenance, and upgrades. For example, the removable mouthpiece allows for easy cleaning and/or swapping with alternative mouthpieces for other users. In addition, the plug and play nature of the interactive airway chamber allows for swapping to other plug in chambers with different sensor suites, interactive airflow devices, and/or resistance and obstruction elements resulting in a variety of specialized interactive airway chambers.

It will further be appreciated that the primary housing 34 and interactive airway chamber 34 as assembled together 250 (FIG. 18) defines a compact, lightweight housing containing an interactive airway elements, a sensor or sensor suite, and a processing module for detecting breathwork characteristics, analyzing the results, and developing a guided routine based on the results, as well as being capable of being used with a variety of respiratory orifice interfaces.

It will further be appreciated that the modular breath tracking and training systems in the spirit of those described herein may be used to measure and analyze breathing patterns using advanced sensors while also offering artificial intelligence (AI) driven, personalized breathing training programs, either as a standalone device or by leveraging connections to the IoT for seamless integration with smart devices and cloud data analytics. Such construction enhances respiratory strength, endurance, and efficiency through targeted exercises and is suitable for users of all levels seeking to improve their breathing and overall health. The modular breath tracking and training systems disclosed herein may also be used in rehabilitation as well as sports training. The respiratory orifice interface fits to a user's face enabling the capture and detection of the amount of air following a bi-directional path.

Certain objects and advantages in conjunction with the embodiments are described herein. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure.

It is also contemplated that various combinations or sub-combinations of the specific features and aspects of the embodiments may be made and still fall within the scope of the invention. Accordingly, it should be understood that various features and aspects of the disclosed embodiments may be combined with or substituted for one another in order to form varying modes of the disclosed invention. Thus, it is intended that the scope of the present invention herein disclosed should not be limited by the particular disclosed embodiments described above.

What is claimed is:

1. A modular breath tracking and training system comprising:

a primary housing with an outermost section having a distal opening and an innermost section having a proximal opening and a passageway from the distal opening to the proximal opening, the primary housing including a plus receiving recess extending into the passageway;

a tech pack including at least one sensor element and an aperture having at least a portion in common with at least a portion of the passageway;

a separable plug including a secondary housing constructed to slip into the plug receiving recess and removably couple to the primary housing with at least a portion secondary housing disposed within the confines of the tech pack aperture, the separable plus defining an interactive airway chamber disposed within at least a portion of the passageway and through which a volume of air may flow bi-directionally;

an airflow responsive element disposed within the separable plug and placed in communication with the at least one sensor element when the plug is disposed at least partially within the plug receiving recess, the airflow responsive element constructed to enter into at least one altered state in response to a volume of air passing through the interactive airway chamber, the at least one altered state being detectable by the at least one sensor element;

at least one swappable respiratory orifice interface with a respiratory orifice side opening and a distal opening, the at least one swappable respiratory orifice interface being constructed to removably couple to the innermost section of the housing to place the distal opening of the at least one swappable respiratory orifice interface in communication with the proximal opening of the primary housing and operable to direct air between the at least one swappable respiratory orifice and the passageway of the primary housing during use;

at least one feedback device in communication with the tech pack, the at least one feedback device constructed to issue a signal corresponding to an actual volume of air passing through the interactive airway chamber based on the altered state of the airflow responsive element or a prompting signal corresponding to a desired volume of air passing through the interactive airway chamber; and a power source disposed within the primary housing and in communication with the tech pack to provide power thereto.

2. The system of claim 1 wherein:

the interactive airway chamber and the plug receiving recess are coaxially aligned when the separable plug is installed in the plug receiving recess.

3. The system of claim 2 wherein:

the tech pack includes at least one printed circuit board assembly including the at least one sensor element and housed within the primary housing.

4. The system of claim 3 wherein:

the at least one printed circuit board assembly defines a ring with a central passage therethrough into which at least a portion of the separable plug is inserted to place the airflow responsive element in communication with the at least one sensor element through a window in the plug, the ring and the airflow responsive element being mounted perpendicularly to a central axis passing through the y of the primary housing; and the airflow responsive element is a fan with a rotational axis coaxially aligned with the central axis passing through the passageway of the primary housing.

5. The system of claim 1 wherein:

the at least one sensor element is constructed to detect a direction of airflow and a flow rate of the actual volume of air passing through the interactive airway chamber, and the at least one feedback device includes an onboard display constructed to display a visual signal corresponding to the direction of the airflow and the flow rate of the actual volume of air passing through the interactive airway chamber.

6. The system of claim 5 wherein:

the onboard display is in the form of a light ring responsive to the airflow direction and the flow rate.

7. The system of claim 1 wherein the airflow responsive element is a fan element having one or more fan blades.

8. The system of claim 1 wherein:

the at least one sensor element is an optical sensor constructed to detect a direction of airflow based on the altered state of the airflow responsive element.

9. The system of claim 1 wherein:

the at least one sensor element is constructed to detect an airflow pressure responsive to a force of an airflow passing through the interactive airflow chamber, and the at least one feedback device includes an onboard display constructed to display a visual signal corresponding to the airflow pressure detected.

10. The system of claim 1 further including:

at least one accelerometer constructed to activate the power source to generate power to the at least one sensor element upon movement of the primary housing.

11. The system of claim 1 wherein:

the at least one swappable respiratory orifice interface is selected from a group consisting of: a mouthpiece, a nasal insert, or a mask.

12. The system of claim 1 further including:

a wireless transmitting device disposed within the primary housing and constructed to transmit one or more airflow related parameters to a remote processing unit and receive one or more training prompts therefrom.

13. The system of claim 12 further including:

a remote processing device in communication with the wireless transmitting device of the primary housing, the remote processing device being programmed to record a set of airflow related parameters responsive to the airflow responsive element, send one or more breathwork exercise prompts to the primary housing unit, and trigger the at least one feedback device.

14. The system of claim 1 wherein:

the at least one sensor element is constructed to detect bi-directional airflow.

15. The system of claim 1 wherein:

the interactive airway chamber is constructed to receive both an inhalation airflow and an exhalation airflow through a common set of ports and passages projecting therethrough.

16. The system of claim 1 wherein:

the primary housing is constructed to removably couple to at least one other swappable respiratory orifice interface of an alternative construction.

17. The system of claim 1 wherein:

the primary housing includes a tapering funnel mouth proximate the distal opening of the outermost section and leading to the plug receiving recess;

the separable plug includes a window passing through the secondary housing;

the plug receiving recess includes a seat disposed within the primary housing to position the airflow responsive element in a direct line of sight communication with the at least one sensor of the tech pack through the window when the separable plug is seated within the plug receiving recess.

18. The system of claim 1 wherein:

the outermost section of the primary housing includes a forward facing light ring diffuser surrounding the distal opening leading to the plug receiving recess; and the tech pack includes a substrate defining the aperture and including a light emitting ring circumferentially aligned with the light ring diffuser, the light emitting ring constructed to emit light out through the forward facing light ring diffuser in response to a volume of airflow passing through the interactive airway chamber.

19. The system of claim 1 wherein;

the secondary housing includes a front section with a first set of fixed spokes and a rear section with a second set of fixed spokes with the airflow responsive element including one or more fan blades rotationally sandwiched between the first and second set of fixed spokes.

20. The system of claim 1 wherein:

the at least one swappable respiratory orifice interface includes one or more bitewings;

a heart rate sensor disposed within the one or more bitewings, the heart rate sensor being placed in communication with the tech pack.

21. The system of claim 1 wherein:

the separable plug and the plug receiving recess include a cooperating alignment feature to ensure a proper orientation of the separable plug relative to the plug receiving recess.

22. The system of claim 1 wherein:

the at least one feedback device is constructed to issue a plurality of feedback signals including a visual signal, an audio signal, and a vibrational signal in response to the actual volume of air passing through the interactive airway chamber.

23. The system of claim 1 wherein:

the passageway through the primary housing is racetrack shaped.

24. The system of claim 1 wherein:

the tech pack includes a substrate defining the aperture and including a light emitting ring constructed to emit light out through a rear facing portion of the primary housing in response to the actual volume of air passing through the interactive airway chamber.

25. The system of claim 1 wherein:

the outermost and innermost sections of the primary housing are detachable from one another to expose the tech pack, the tech pack being constructed to be swapped out with an alternative tech pack having at least one different sensor.

26. A modular breath tracking and training system comprising:

a primary housing having a distal opening and a proximal opening and a passageway from the distal opening to the proximal opening, the primary housing including an insert receiving s extending into the passageway and terminating in a seat;

a sensor suite mounted on a substrate with at least one sensor constructed to detect a volume of airflow in either direction along the passageway, the substrate further including an aperture having at least a portion coaxially aligned with and in common with at least a portion of the passageway;

a swappable insert including a secondary housing removably inserted into the insert receiving recess to abut an interior end of the secondary housing against the seat and position at least a portion of the secondary housing within the confines of the substrate aperture, the swappable insert defining an interactive airway chamber having a window and disposed within at least a portion of the passageway through which a volume of air may flow bi-directionally;

an airflow responsive element disposed within the insert and placed in communication with the at least one sensor through the window of the interactive airway chamber when the insert is seated within the receiving recess, the airflow responsive element constructed to enter into at least one altered state in response to a volume of air passing through the interactive airway chamber, the at least one altered state being detectable by the at least one sensor;

at least one swappable respiratory orifice interface constructed to removably couple to the proximal opening of the housing and operable to channel a volume of air between the at least one swappable respiratory orifice and the interactive airway chamber during use;

an onboard light ring in communication with the sensor suite, the light ring constructed to issue a visual signal corresponding to an actual or a desired volume of air passing through the interactive airway chamber; and a power source disposed within the primary housing and in communication with the suite to provide power thereto allowing detection of a volume of air through the interactive airway chamber by the at least one sensor and generation of one or more visual signals emitted by the light ring while the primary housing and swappable insert are supported solely by a user engaging the at least one swappable respiratory orifice with their mouth and conducting a set of breathwork exercises.

27. A modular breath tracking and training system comprising:

a primary housing having a distal opening and a proximal opening and a passageway from the distal opening to the proximal opening, the primary housing including an insert receiving recess extending into the passageway;

a swappable insert including a sensor suite including at least one sensor and defining an interactive airway chamber, the swappable insert removably slipped into the insert receiving recess to place at least a portion of the interactive airway chamber in communication with at least a portion of the passageway through which a volume of air may flow bi-directionally;

at least one airflow responsive element disposed in communication with the interactive airway chamber and in communication with the at least one sensor, the at least one sensor being constructed to detect a reaction by the airflow responsive element in response to a volume of air passing through the interactive airway chamber;

at least one swappable respiratory orifice interface with a respiratory orifice side opening and an opposing distal opening constructed to removably couple to the proximal opening of the primary housing to direct air between the at least one swappable respiratory orifice and the passageway of the primary housing during use;

an onboard signal generating device in communication with the sensor suite, the signal generating device constructed to issue a feedback signal corresponding to an actual volume of air based on the reaction of the airflow responsive element or a prompting signal corresponding to a desired volume of air to be passed through the interactive airway chamber; and a power source disposed within the primary housing and in communication with the sensor suite and onboard signal generating device to provide power thereto to enter a ready state allowing the generation of one or more signals corresponding to a volume of air passing through the interactive airway chamber while the primary housing and swappable insert are supported solely by the user engaging the at least one swappable respiratory orifice with their mouth and conducting a set of breathwork exercises.

* * * * *